United States Patent
Old et al.

(10) Patent No.: US 6,706,755 B2
(45) Date of Patent: Mar. 16, 2004

(54) CYCLOPENTANE HEPTAN(ENE) ACYL SULFONAMIDE, 2-ALKYL OR 2-ARYLALKYL, OR 2-HETEROARYLALKENYL DERIVATIVES AS THERAPEUTIC AGENTS

(75) Inventors: David W. Old, Irvine, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/228,412

(22) Filed: Aug. 26, 2002

(65) Prior Publication Data

US 2003/0027846 A1 Feb. 6, 2003

Related U.S. Application Data

(63) Continuation of application No. 09/880,272, filed on Jun. 13, 2001, now Pat. No. 6,476,064.

(51) Int. Cl.[7] ................... A61K 31/5575; C07C 311/51
(52) U.S. Cl. ................ 514/438; 514/604; 549/65; 564/94; 564/98
(58) Field of Search ................. 514/438, 604; 549/65; 564/94, 98

(56) References Cited

U.S. PATENT DOCUMENTS

| | | |
|---|---|---|
| 3,954,741 A | 5/1976 | Schaaf et al. |
| 4,024,179 A * | 5/1977 | Bindra et al. ............... 560/53 |
| 4,994,274 A | 2/1991 | Chan et al. |
| 5,028,624 A | 7/1991 | Chan et al. |
| 5,034,413 A | 7/1991 | Chan et al. |
| 5,446,041 A | 8/1995 | Chan et al. |

FOREIGN PATENT DOCUMENTS

DE 28 25 855 A1 6/1977

OTHER PUBLICATIONS

Wang, Chem. Pharm. Bull. 48(9) 1332 21(2000).*
Bito, L.Z., *Biological Protection with Prostaglandins*, "Prostaglandins and Related Compounds as Potential Ocular Therapeutic Agents", vol. 1, Chapter 18, 1985, pp. 231–252.
Bito, L.Z., *Glaucoma, Applied Pharmacology in the Medical Treatment*, "Prostaglandins, Other Eicosanoids, and Their Derivatives as Potential Antiglaucoma Agents",1984, Chapter 20, pp. 477–505.
Nilsson et al, Invest. Ophthalmol. Vis. Sci. (suppl), 284 (1987), Arvo Abstracts 9–6:00.
Bito, L.Z., Arch. Ophthalmol. "Prostaglandins" "Old Concepts and New Perspectives", vol. 105, pp. 1036–1039 (1987).
Siebold et al, Prodrug 5 3, "Esterified protaglandin shows 'potent' promise",1989.
Schaaf, T.K. et al, "Synthesis and Biological Activity of Carboxyl–Terminus Modified Prostaglandin Analogues", J. Med. Chem. 1979, 22, 1340–1346.
Wang et al, *J. Med Chem*, 2000, 43, 945–952.

* cited by examiner

Primary Examiner—Robert Gerstl
(74) Attorney, Agent, or Firm—Brent A. Johnson; Martin A. Voet; Robert J. Baran

(57) ABSTRACT

The present invention provides a method of treating ocular hypertension or glaucoma which comprises administering to an animal having ocular hypertension or glaucoma therapeutically effective amount of a compound represented by the general formula I;

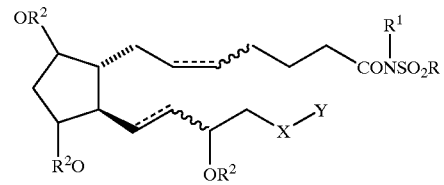

wherein a hatched line represents the α configuration, a triangle represents the β configuration, a straight line, e.g. at the 9, 11 or 15 position represents either the α or β configuration, a dotted line represents the presence or absence of a double bond; a wavy line represents a cis or trans bond;

X is O, S, NH or $(CH_2)_n$;
n is 0 or an integer of from 1 to 4;
Y is $C_1$–$C_5$ n-alkyl, $C_3$–$C_7$ cycloalkyl, phenyl, furanyl, thienyl, pyridinyl, thiazolyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $N(R^2)_2$, $CO_2R^2$ and $OR^2$;
Z is $(CH_2)_n$ or a covalent bond;
R is $C_1$–$C_6$ lower alkyl or Z-$CF_3$ or mesylate or triflate;
$R^1$ is H, $R^2$ or $COR^2$; and
$R^2$ is H or $C_1$–$C_5$ lower alkyl or 9, 11 or 15 esters thereof.

11 Claims, 2 Drawing Sheets

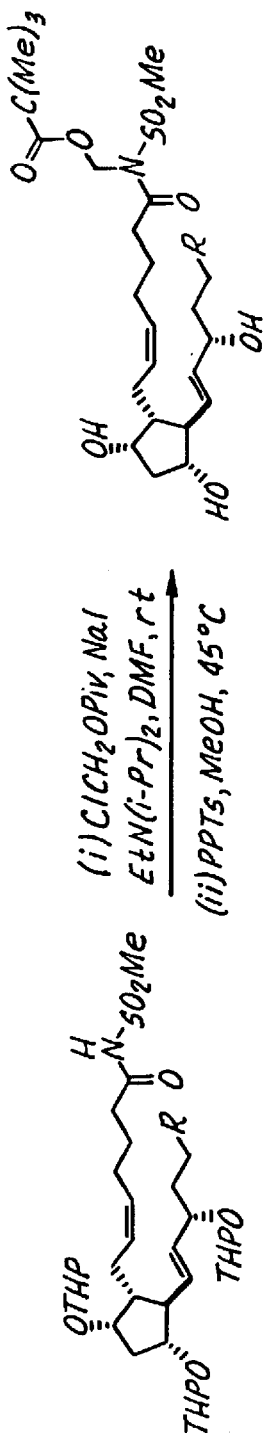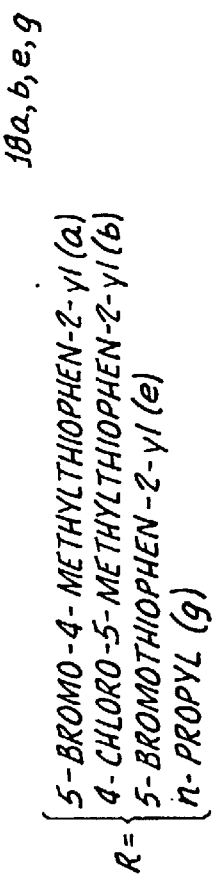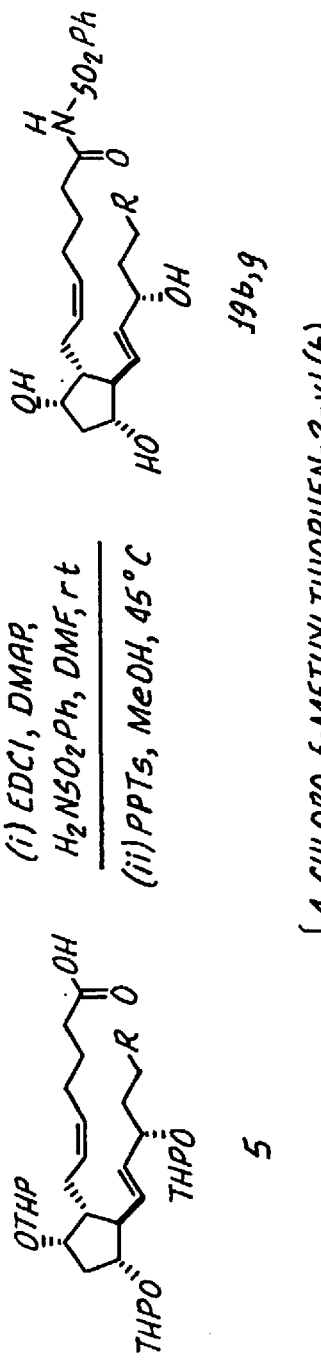
Fig. 3.
Fig. 4.

CYCLOPENTANE HEPTAN(ENE) ACYL SULFONAMIDE, 2-ALKYL OR 2-ARYLALKYL, OR 2-HETEROARYLALKENYL DERIVATIVES AS THERAPEUTIC AGENTS

CROSS REFERENCE TO RELATED APPLICATIONS

This patent application is a continuation of U.S. patent application Ser. No. 09/880,272, filed Jun. 13, 2001 now U.S. Pat. No. 6,476,064.

BACKGROUND OF THE INVENTION

1. Field of the Invention

The present invention relates to cyclopentane heptan(ene) acyl sulfonamide, 2-alkyl or 2-arylalkyl, or 2-heteroarylalkenyl derivatives as therapeutic agents, e.g. such agents are potent ocular hypotensives that are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

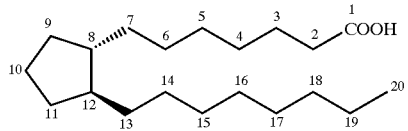

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175,476 (filed Dec. 29, 1993). Similarly, 11,15- 9,15 and 9,11-diesters of prostaglandins, for example 11,15-dipivaloyl $PGF_{2\alpha}$ are known to have ocular hypotensive activity. See the co-pending patent applications U.S. Ser. Nos. 385,645 (filed Jul. 7, 1989, now U.S. Pat. No. 4,994,274), U.S. Ser. No. 584,370 (filed Sep. 18, 1990, now U.S. Pat. No. 5,028,624) and U.S. Ser. No. 585,284 (filed Sep. 18, 1990, now U.S. Pat. No. 5,034,413). The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I

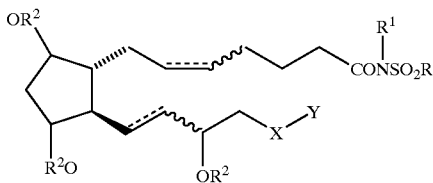

wherein a hatched line represents the α configuration, a triangle represents the β configuration, a straight line, e.g. at the 9, 11 or 15 position, represents either the α or β configuration, a dotted line represents the presence or absence of a double bond; a wavy line represents a cis or trans bond;

X is O, S, NH or $(CH_2)_n$;

n is 0 or an integer of from 1 to 4;

Y is $C_1$–$C_5$ n-alkyl, $C_3$–$C_7$ cycloalkyl, phenyl, furanyl, thienyl, pyridinyl, thiazolyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $N(R^2)_2$, $CO_2R^2$ and $OR^2$;

Z is $(CH_2)_n$ or a covalent bond;

R is $C_1$–$C_6$ lower alkyl, benzyl, or Z—$CF_3$ or mesylate or triflate;

$R^1$ is H, $R^2$ or $COR^2$; and $R^2$ is H or $C_1$–$C_5$ lower alkyl or 9, 11 or 15 esters thereof.

In a still further aspect, the present invention relates to a pharmaceutical product, comprising a container adapted to dispense its contents in a metered form; and an ophthalmic solution therein, as hereinabove defined.

Finally, certain of the compounds represented by the above formula, disclosed below and utilized in the method of the present invention are novel and unobvious.

BRIEF DESCRIPTION OF THE DRAWING FIGURES

FIG. 3 is a schematic of the chemical synthesis of certain compounds of the invention as disclosed in Examples 40, 42, 44 and 46.

FIG. 4 is a schematic of the chemical synthesis of certain compounds of the invention as disclosed in Examples 47 and 48.

DETAILED DESCRIPTION OF THE INVENTION

Figure 1:
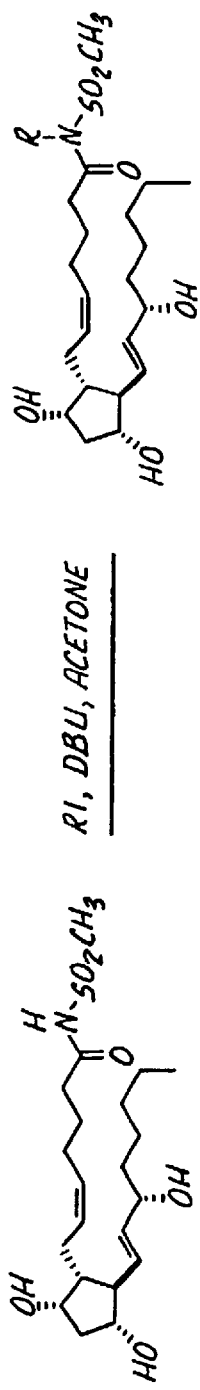
FIG. 1 is a schematic of the chemical synthesis of certain compounds of the invention as disclosed in Examples 5 and 6.

The present invention relates to the use of cyclopentane heptan(ene) acyl sulfonamide, 2-alkyl or 2-arylalkyl, or 2-heteroarylalkenyl derivatives as therapeutic agents as ocular hypotensives. The compounds used in accordance with the present invention are encompassed by the following structural formula I:

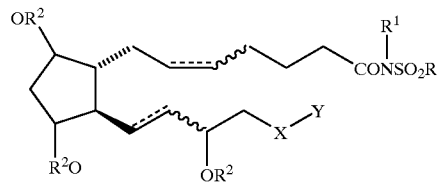

A preferred group of the compounds of the present invention includes compounds that have the following structural formula II:

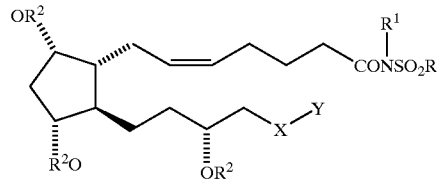

Another preferred group includes compounds having the formula III:

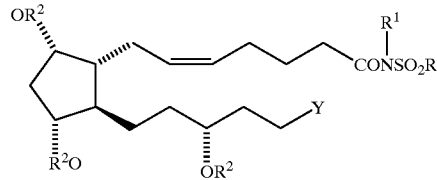

In the above formulae, the substituents and symbols are as hereinabove defined.

In the above formula:

X is preferably $CH_2$.

Y is preferably selected from the group consisting of n-propyl, thienyl and halo or lower $C_1$ to $C_4$ alkyl substituted derivatives of thienyl.

Z is preferably a covalent bond.

R is preferably selected from the group consisting of methyl, ethyl, n-propyl, n-butyl, benzyl, $CF_3$, mesylate or triflate.

$R^1$ is preferably selected from the group consisting of H, methyl, ethyl, acetyl or pivaloyl.

$R^2$ is preferably H.

The above compounds of the present invention may be prepared by methods that are known in the art or according to the working examples below. The compounds, below, are especially preferred representatives, of the compounds of the present invention.

N-{(Z)-7-[(1R,2R,3R,5S)-3,5-Dihydroxy-2-((S)-(E)-3-hydroxyoct-1-enyl)cyclopentyl]-hept-5-enoyl}methanesulfonamide Ethanesulfonic acid {(Z)-7-[(1R,2R,3R,5S)-3,5-dihydroxy-2-((S)-(E)-3-hydroxyoct-1-enyl)cyclopentyl]hept-5-enoyl}amide Ethanesulfonic acid {(Z)-7-[(1R,2R,3R,5S)-3,5-dihydroxy-2-((R)-(E)-3-hydroxyoct-1-enyl)cyclopentyl]hept-5-enoyl}amide Propane-1-sulfonic acid {(Z)-7-[(1R,2R,3R,5S)-3,5-dihydroxy-2-((S)-(E)-3-hydroxyoct-1-enyl)cyclopentyl]hept-5-enoyl}amide Propane-1-sulfonic acid {(Z)-7-[(1R,2R,3R,5S)-3,5-dihydroxy-2-((R)-(E)-3-hydroxyoct-1-enyl)cyclopentyl]hept-5-enoyl}amide Butane-1-sulfonic acid {(Z)-7-[(1R,2R,3R,5S)-3,5-dihydroxy-2-((S)-(E)-3-hydroxyoct-1-enyl)cyclopentyl]hept-5-enoyl}amide Butane-1-sulfonic acid {(Z)-7-[(1R,2R,3R,5S)-3,5-dihydroxy-2-((R)-(E)-3-hydroxyoct-1-enyl)cyclopentyl]hept-5-enoyl}amide N-{(Z)-7-[(1R,2R,3R,5S)-3,5-Dihydroxy-2-((S)-(E)-3-hydroxyoct-1-enyl)cyclopentyl]-hept-5-enoyl}N-methylmetbanesulfonamide N-{(Z)-7-[(1R,2R,3R,5S)-3,5-Dihydroxy-2-((S)-(E)-3-hydroxyoct-1-enyl)cyclopentyl]-hept-5-enoyl}N-ethylmethanesulfonamide N-{(Z)-7-[(1R,2R,3R,5S)-3,5-Dihydroxy-2-((S)-(E)-3-hydroxy-5-phenylpent-1-enyl)cyclopentyl]-hept-5-enoyl}methanesulfonamide 2,2-Dimethylpropionic acid (1R,2R,3R,5S)-4-hydroxy-2-((S)-(E)-3-hydroxyoct-1-enyl)-3-((Z)-7-methanesulfonylamino-7-oxohept-2-enyl)cyclopentyl ester N-{(Z)-7-[(1R,2R,3R,5S)-3,5-Dihydroxy-2-((S)-(E)-3-hydroxyoct-1-enyl)cyclopentyl]-hept-5-enoyl}-1,1,1-trifluoromethanesulfonamide N-{(E)-7-[(1R,2R,3R,5S)-3,5-Dihydroxy-2-((S)-(E)-3-hydroxy-5-phenylpent-1-enyl)-cyclopentyl]hept-5-enoyl}methanesulfonamide Ethanesulfonic acid ((Z)-7-{(1R,2R,3R,5S)-2-[(S)-(E)-5-(4-bromo-5-methylthiophen-2-yl)-3-hydroxypent-1-enyl]-3,5-dihydroxycyclopentyl}hept-5-enoyl)amide N-((Z)-7-{(1R,2R,3R,5S)-2-((S)-(E)-5-(5-Bromo-4-methylthiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-((S)-(E)-5-(5-bromo-4-methylthiophen-2-yl)-3-hydroxypent-1-enyl)-3,5-dihydroxycyclopentyl]hept-5-enoyl}amide N-((Z)-7-{(1R,2R,3R,5S)-2-[((S)-(E)-5-(5-Bromo-4-methylthiophen-2-yl)-3-hydroxypent-1-enyl)-3,5-dihydroxycyclopentyl]hept-5-enoyl}-1,1,1-trifluoromethanesulfonamide N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-[((S)-(E)-5-(4-chloro-5-methylthiophen-2-yl)-3-hydroxypent-1-enyl)-3,5-dihydroxycyclopentyl]hept-5-enoyl}amide N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}-1,1,1-trifluoromethanesulfonamide N-((Z)-7-{(1R,2R,3R,5S)-3,5-Dihydroxy-2-[((S)-(E)-3-hydroxy-5-(2-methylthiophen-3-yl)pent-1-enyl)cyclopentyl}hept-5-enoyl)methanesulfonamide Ethanesulfonic acid ((Z)-7-{(1R,2R,3R,5S)-3,5-dihydroxy-2-[((S)-(E)-3-hydroxy-5-(2-methylthiophen-3-yl)pent-1-enyl]cyclopentyl}hept-5-enoyl)amide N-((Z)-7-{(1R,2R,3R,5S)-3,5-Dihydroxy-2-[((S)-(E)-3-hydroxy-5-(2-methylthiophen-3-yl)pent-1-enyl]cyclopentyl}hept-5-enoyl)-1,1,1-trifluoromethanesulfonamide N-((Z)-7-{(1R,2R,3R,5S)-3,5-Dihydroxy-2-[((S)-(E)-3-hydroxy-5-(2-methylthiophen-3-yl)pent-1-enyl)cyclopentyl}heptanoyl)methanesulfonamide Ethanesulfonic acid ((Z)-7-{(1R,2R,3R,5S)-3,5-dihydroxy-2-[((S)-(E)-3-hydroxy-5-(2-methylthiophen-3-yl)pent-1-enyl]cyclopentyl}heptanoyl)amide N-((Z)-7-{(1R,2R,3R,5S)-3,5-Dihydroxy-2-[((S)-(E)-3-hydroxy-5-(2-methylthiophen-3-yl)pent-1-enyl]cyclopentyl}heptanoyl)-1,1,1-trifluoromethanesulfonamide N-((Z)-7-{(1R,2R,3R,5S)-2-[((S)-(E)-5-(5-Chlorothiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-[((S)-(E)-5-(5-chlorothiophen-2-yl)-3-hydroxypent-1-enyl)-3,5-dihydroxycyclopentyl]hept-5-enoyl}amide N-((Z)-7-{(R,2R,3R,5S)-2-[((S)-(E)-5-(5-Chlorothiophen-2-yl)-3-hydroxypent-1-enyl)-3,5-dihydroxycyclopentyl]hept-5-enoyl}-1,1,1-trifluoromethanesulfonamide N-((Z)-7-{(1R,2R,3R,5S)-3,5-Dihydroxy-2-[((S)-(E)-3-hydroxy-5-(5-iodothiophen-2-yl)pent-1-enyl]cyclopentyl}heptanoyl)methanesulfonamide Ethanesulfonic acid ((Z)-7-{(1R,2R,3R,5S)-3,5-dihydroxy-2-[((S)-(E)-3-hydroxy-5-(5-iodothiophen-2-yl)pent-1-enyl]cyclopentyl}heptanoyl)amide N-((Z)-7-{(1R,2R,3R,5S)-3,5-Dihydroxy-2-[((S)-(E)-3-hydroxy-5-(5-iodothiophen-2-yl)pent-1-enyl]cyclopentyl}heptanoyl)-1,1,1-trifluoromethanesulfonamide N-((Z)-7-{(1R,2R,3R,5S)-2-[((S)-(E)-5-(5-Bromothiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-[((S)-(E)-5-(5-bromothiophen-2-yl)-3-hydroxypent-1-enyl)-3,5-dihydroxycyclopentyl]hept-5-enoyl}amide N-((Z)-7-{(1R,2R,3R,5S)-2-[((S)-(E)-5-(5-Bromothiophen-2-yl)-3-hydroxypent-1-enyl)-3,5-dihydroxycyclopentyl]hept-5-enoyl}-1,1,1-trifluoromethanesulfonamide Acetic acid ({(Z)-7-[(1R,2R,3R,5S)-3,5-dihydroxy-2-((S)-(E)-3-hydroxyoct-1-enyl)-cyclopentyl]hept-5-enoyl}methanesulfonylamino)methyl ester 2,2-Dimethylpropionic acid ({(Z)-7-[(1R,2R,3R,5S)-3,5-dihydroxy-2-((S)-(E)-3-hydroxyoct-1-enyl)-cyclopentyl]hept-5-enoyl}methanesulfonylamino)methyl ester Acetic acid [((Z)-7-{(1R,2R,3R,5S)-2-[((S)-(E)-5-(5-bromo-4-methylthiophen-2-yl)-3-hydroxypent-1-enyl)-3,5-dihydroxycyclopentyl}hept-5-enoyl)methanesulfonylamino] methyl ester 2,2-Dimethylpropionic acid [((Z)-7-{(1R,2R,3R,5S)-2-[((S)-(E)-5-(5-bromo-4-methylthiophen-2-yl)-3-hydroxypent-1-enyl)-3,5-dihydroxycyclopentyl}hept-5-enoyl)methanesulfonyl-amino] methyl ester Acetic acid [((Z)-7-{(1R,2R,3R,5S)-2-[((S)-(E)-5-(4-chloro-5-methylthiophen-2-yl)-3-hydroxypent-1-enyl)-3,5-dihydroxycyclopentyl}hept-5-enoyl)methanesulfonylamino] methyl ester 2,2-Dimethylpropionic acid [((Z)-7-{(1R,2R,3R,5S)-2-[((S)-(E)-5-(4-chloro-5-methyl-thiophen-2-yl)-3-hydroxypent-1-enyl)-3,5-dihydroxycyclopentyl}hept-5-enoyl)methane-sulfonyl-amino] methyl ester Acetic acid [((Z)-7-{(1R,2R,3R,5S)-2-[((S)-(E)-5-(5-bromothiophen-2-yl)-3-hydroxypent-1-enyl)-3,5-dihydroxycyclopentyl}hept-5-enoyl)methanesulfonylamino] methyl ester 2,2-Dimethylpropionic acid [((Z)-7-{(1R,2R,3R,5S)-2-[((S)-(E)-5-(5-bromothiophen-2-yl)-3-hydroxypent-1- enyl)-3,5-dihydroxycyclopentyl}hept-5-enoyl) methanesulfonyl-amino] methyl ester {3-[(1R,2S,3R)-3-Hydroxy-2-((S)-(E)-3-hydroxyoct-1-enyl)-5-oxocyclopentylsulfanyl]propylsulfanyl}acetic acid methyl ester {3-[(1R,2S,3R)-3-Hydroxy-2-((S)-(E)-3-hydroxyoct-1-enyl)-5-oxocyclopentylsulfanyl]propylsulfanyl}acetic acid {3-[(1R,2S,3R)-3-Hydroxy-2-((S)-(E)-3-hydroxyoct-1-enyl)-5-oxocyclopentylsulfanyl]propylsulfanyl}acetic acid isopropyl ester (3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid methyl ester (3-{(1R,2S,3R)-3-Hydroxy-2-[(E)-4-hydroxy-4-(1-propylcyclobutyl)but-1-enyl]-5-oxocyclopentylsulfanyl}propylsulfanyl)acetic acid N-{(Z)-7-[(1R,2R,3R,5S)-3,5-Dihydroxy-2-((S)-(E)-3-hydroxyoct-1-enyl)cyclopentyl]-hept-5-enoyl}benzenesulfonamide N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}benzenesulfonamide Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Figure 2:
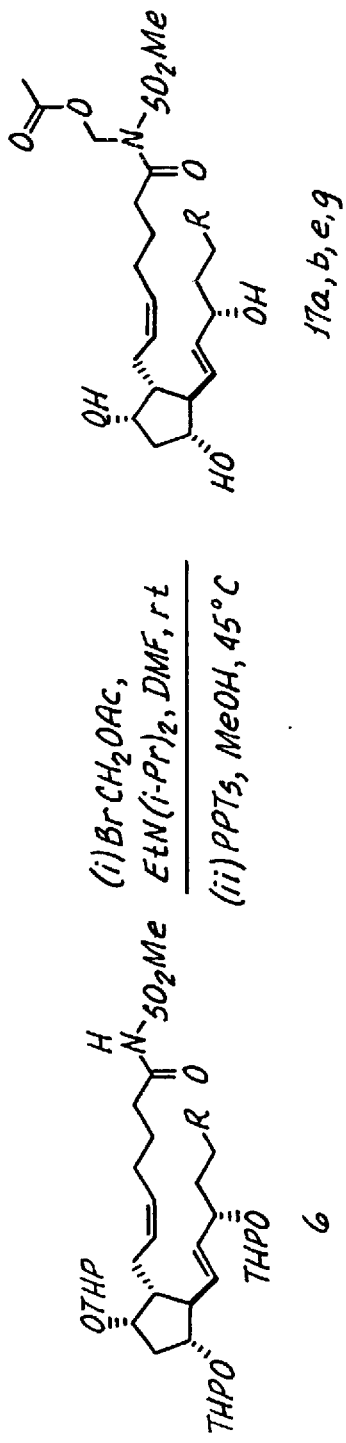
FIG. 2 is a schematic of the chemical synthesis of certain compounds of the invention as disclosed in Examples 39, 41, 43 and 45.

The invention is further illustrated by the following non-limiting Examples, which are summarized in the reaction schemes of FIGS. 1 through 3 wherein the compounds are identified by the same designator in both the Examples and the Figures.

EXAMPLE 1

N-{(Z)-7-[(1R,2R,3R,5S)-3,5-Dihydroxy-2-((S)-(E)-3-hydroxyoct-1-enyl)cyclopentyl]-hept-5-enoyl}methanesulfonamide Prepared in accordance with the procedures described in Schaaf, T. K., Hess, H. -J. *J. Med. Chem.* 1979, 22, 1340–1346.

Scheme 1

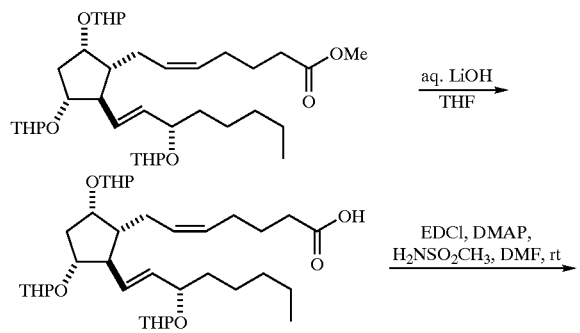

-continued

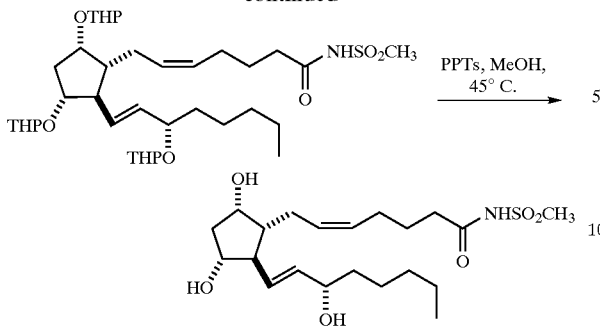

Alternatively, the title compound could be synthesized from tris-THP-prostaglandin $F_{2\alpha}$ methyl ester as follows (see Scheme 1):

Step 1: Saponification of the Ester

Lithium hydroxide (6.8 mL of a 1.0 N solution in $H_2O$, 6.8 mmol) was added to a solution of tris-THP-prostaglandin $F_{2\alpha}$, methyl ester (1.05 g, 1.69 mmol) in THF (16 mL). After stirring 18 h at room temperature the reaction mixture was concentrated in vacuo. The residue was diluted with $H_2O$, acidified with 1 N HCl and extracted with $CH_2Cl_2$ (2×). The combined extracts were washed with brine, dried ($Na_2SO_4$) filtered and concentrated in vacuo. Purification by flash column chromatography (silica gel, 33% EtOAc/Hex) afforded 940 mg (92%) of tris-THP $PGF_{2\alpha}$.

Step 2: Preparation of the Tris-THP Acylsulfonamide

Tris-THP $PGF_{2\alpha}$ (495 mg, 0.816 mmol), 1-(3-dimethylaminopropyl)-3-ethylcarbodiimide hydrochloride (EDCI) (220 mg, 1.15 mmol), 4-dimethyl-aminopyridine (DMAP) (125 mg, 1.02 mmol) and methanesulfonamide (235 mg, 2.47 mmol) were dissolved in DMF (3.4 mL) and the resulting solution was stirred at room temperature under an atmosphere of nitrogen. After 16 h the solution was diluted with EtOAc and washed with 1 N aqueous HCl (3×) and brine (1×), then dried ($Na_2SO_4$), filtered and concentrated in vacuo. Purification by flash column chromatography (silica gel, 45% EtOAc/Hex) afforded 468 mg (84%) of tris-THP $PGF_{2\alpha}$ methanesulfonamide.

Step 3: Deprotection of the Tris-THP Acylsulfonamide

Pyridinium p-toluenesulfonate (PPTs) (20 mg, 0.080 mmol) was added to a solution of tris-THP $PGF_{2\alpha}$ methanesulfonamide (468 mg, 0.684 mmol) in MeOH (6.5 mL). The solution was heated at 45° C. under an atmosphere of nitrogen. After 16 h, the reaction mixture was cooled then concentrated in vacuo to afford a crude oil. Flash column chromatography (silica gel, EtOAc, then 2% MeOH in EtOAc) gave 152 mg (51%) of the title compound.

EXAMPLE 2

Ethanesulfonic acid {(Z)-7-[(1R,2R,3R,5S)-3,5-Dihydroxy-2-((S)-(E)-3-hydroxyoct-1-enyl)cyclopentyl]hept-5-enoyl}amide and Ethanesulfonic acid {(Z)-7-[(1R,2R,3R,5S)-3,5-Dihydroxy-2-((R)-(E)-3-hydroxyoct-1-enyl)cyclopentyl]hept-5-enoyl}amide The title compounds were prepared in accordance with the procedures described in Schaaf, T. K., Hess, H. -J. *J. Med. Chem.* 1979, 22, 1340–1346, with the following exceptions: methanesulfonamide was replaced with ethanesulfonamide; the bicyclic lactol was used as a 1:1 mixture of epimeric 15R and 15S alcohols (prostaglandin numbering used, see Scheme 2); the 15R and 15S alcohols were separated during chromatography at the end of the synthetic sequence to afford the title compounds.

Scheme 2

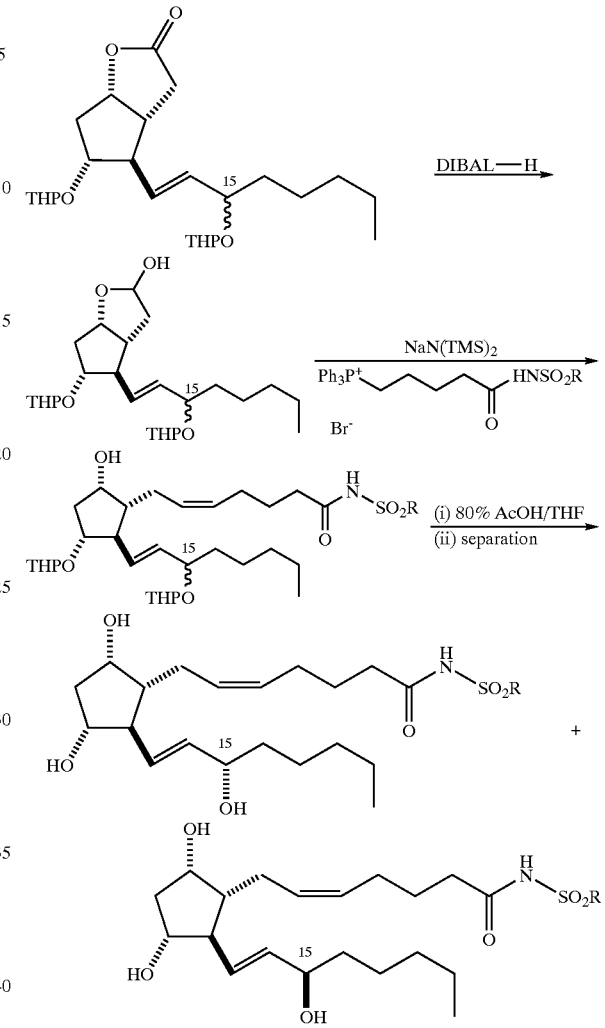

EXAMPLE 3

Propane-1-sulfonic acid {(Z)-7-[(1R,2R,3R,5S)-3,5-Dihydroxy-2-((S)-(E)-3-hydroxyoct-1-enyl)cyclopentyl]hept-5-enoyl}amide and propane-1-sulfonic acid {(Z)-7-[(1R,2R,3R,5S)-3,5-Dihydroxy-2-((R)-(E)-3-hydroxyoct-1-enyl)cyclopentyl]hept-5-enoyl}amide The title compounds were prepared in accordance with the procedures described in Schaaf, T. K., Hess, H. -J. *J. Med. Chem.* 1979, 22, 1340–1346, with the following exceptions: methanesulfonamide was replaced with propane-1-sulfonamide; the bicyclic lactol was used as a 1:1 mixture of epimeric 15R and 15S alcohols (prostaglandin numbering used, see Scheme 2); the 15R and 15S alcohols were separated during chromatography at the end of the synthetic sequence to afford the title compounds.

EXAMPLE 4

Butane-1-sulfonic acid {(Z)-7-[(1R,2R,3R,5S)-3,5-Dihydroxy-2-((S)-(E)-3-hydroxyoct-1-enyl)cyclopentyl]hept-5-enoyl}amide and Butane-1-sulfonic acid {(Z)-7-[(1R,2R,3R,5S)-3,5-Dihydroxy-2-((R)-(E)-3-hydroxyoct-1-enyl)cyclopentyl]hept-5-enoyl}amide The title compounds were prepared in accordance with the procedures described in Schaaf, T. K., Hess, H. -J. *J.*

Med. Chem. 1979, 22, 1340–1346, with the following exceptions: methanesulfonamide was replaced with butane-1-sulfonamide; the bicyclic lactol was used as a 1:1 mixture of epimeric 15R and 15S alcohols (prostaglandin numbering used, see Scheme 2); the 15R and 15S alcohols were separated during chromatography at the end of the synthetic sequence to afford the title compounds.

EXAMPLE 5
N-{(Z)-7-[(1R,2R,3R,5S)-3,5-Dihydroxy-2-((S)-(E)-3-hydroxyoct-1-enyl)cyclopentyl]-hept-5-enoyl}-N-methylmethanesulfonamide Methyl iodide (38 μL, 0.61 mmol) and DBU (45 μL, 0.30 mmol) were added to a solution of N-{(Z)-7-[(1R,2R,3R,5S)-3,5-Dihydroxy-2-((S)-(E)-3-hydroxyoct-1-enyl)cyclopentyl]hept-5-enoyl}methanesulfonamide (44 mg, 0.10 mmol) in acetone (1.5 mL). After stirring for 2.5 h at room temperature, the reaction was diluted with EtOAc, washed with water (2×) and brine then concentrated in vacuo to afford the title compound. See FIG. 1.

EXAMPLE 6
N-{(Z)-7-[(1R,2R,3R,5S)-3,5-Dihydroxy-2-((S)-(E)-3-hydroxyoct-1-enyl)cyclopentyl]-hept-5-enoyl}-N-ethylmethanesulfonamide The title compound was prepared in accordance with the procedure of example 5, replacing methyl iodide with ethyl iodide.

EXAMPLE 7
N-{(Z)-7-[(1R,2R,3R,5S)-3,5-Dihydroxy-2-((S)-(E)-3-hydroxy-5-phenylpent-1-enyl)cyclopentyl]hept-5-enoyl}methanesulfonamide Step 1: Global Silylation of 17-Phenyl $PGF_{2\alpha}$ 2,6-Lutidine (0.940 mL, 8.07 mmol) and tert-butyldimethylsilyl chloride (1.22 g, 8.07 mmol) were added to a solution of 17-phenyl $PGF_{2\alpha}$ (521 mg, 1.34 mmol) in DMF (13.4 mL). After stirring overnight at room temperature, the reaction was diluted with EtOAc then washed with water (3×) and brine (2×) and concentrated in vacuo. Purification of the residue by flash column chromatography (silica gel, 5% EtOAc/Hex) afforded 1.06 g (93%) of tetra-TBDMS-17-phenyl $PGF_{2\alpha}$.

Step 2: Preparation of the Tris-TBDMS acid

A solution of potassium carbonate (345 mg, 2.50 mmol) in $H_2O$ (3.5 mL) was added to a solution of tetra-TBDMS-17-phenyl $PGF_{2\alpha}$ (1.06 g, 1.25 mmol) in MeOH (15.6 mL) and THF (5.2 mL). After 1 h, the reaction mixture was acidified with 1 N HCl and extracted with $CH_2Cl_2$ (3×). The combined extracts were dried ($Na_2SO_4$), filtered and concentrated in vacuo to afford 912 mg (100%) of tris-TBDMS-17-phenyl $PGF_{2\alpha}$.

Step 3: Preparation of the Tris-TBDMS Acylsulfonamide

Methanesulfonamide (519 mg, 6.25 mmol), DMAP (153 mg, 1.25 mmol) and DCC (1.29 g, 6.25 mmol) were added to a solution of tris-TBDMS-17-phenyl $PGF_{2\alpha}$ (912 mg, 1.25 mmol) in $CH_2Cl_2$ (100 mL). The solution was stirred at room temperature overnight, then concentrated in vacuo. The residue was diluted with EtOAc and the solid urea by-product was removed by filtration. The filtrate was concentrated in vacuo and the residue was purified twice by flash column chromatography (silica gel, 25% EtOAc/Hex) to afford 176 mg (17%) of the tris-TBDMS acylsulfonamide.

Step 4: Desilylation of the Tris-TBDMS Acylsulfonamide

Hydrogen fluoride-pyridine (288 μL) was added to a solution of the compound obtained in step 1 above (176 mg, 0.241 mmol) in THF (3.6 mL) at 0° C. under $N_2$. After 2 h, additional HF-pyridine (288 μL) was added and stirring was continued at 0° C. After 1 h, additional HF-pyridine (288 μL) was added and stirring was continued at 0° C. for 40 min, then the reaction mixture was allowed to warm to room temperature. The solution was then diluted with EtOAc and neutralized with saturated $NaHCO_3$. The layers were separated and the aqueous phase was extracted with $CHCl_3$ (2×). The combined organic layers were concentrated in vacuo. The residue was purified by flash chromatography (silica gel, 5% MeOH/EtOAc) to afford 22 mg (20%) of the title compound. This method of this Example is shown in Scheme 3.

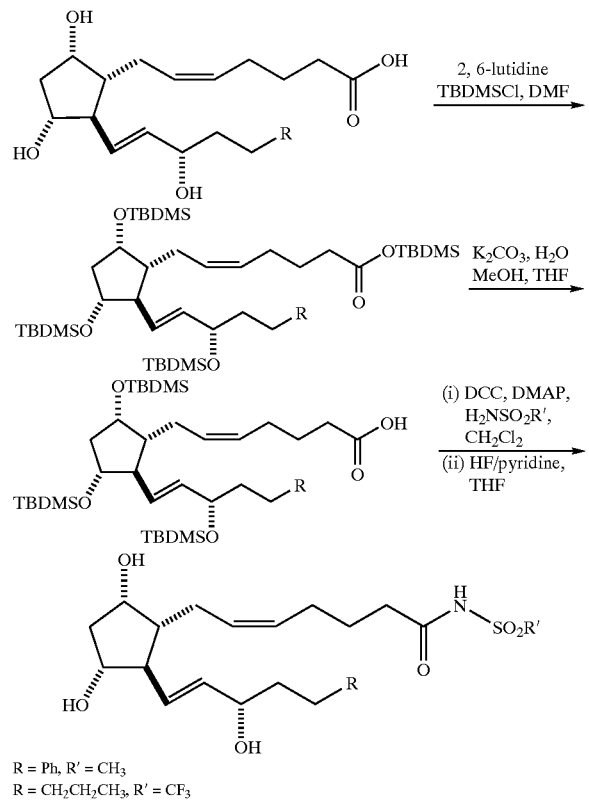

EXAMPLE 8
N-{(Z)-7-[(1R,2R,3R,5S)-3,5-Dihydroxy-2-((S)-(E)-3-hydroxyoct-1-enyl)cyclopentyl]-hept-5-enoyl}-1,1,1-trifluoromethanesulfonamide Step 1: Global Silylation of $PGF_{2\alpha}$ In accordance with the procedure described in example 7, step 1, the use of $PGF_{2\alpha}$ gave tetra-TBDMS-$PGF_{2\alpha}$ Step 2: Preparation of the Tris-TBDMS acid In accordance with the procedure described in example 7, step 2, the use of tetra-TBDMS-$PGF_{2\alpha}$ gave tris-TBDMS-$PGF_{2\alpha}$.

Step 3: Preparation of the Tris-TBDMS Acylsulfonamide

In accordance with the procedure described in example 7, step 3, the use of tris-TBDMS-$PGF_{2\alpha}$ and trifluoromethanesulfonamide afforded tris-TBDMS-$PGF_{2\alpha}$ trifluoromethanesulfonamide.

Step 4: Desilylation of the Tris-TBDMS Acylsulfonamide

In accordance with the procedure described in example 7, step 4, the use of tris-TBDMS-$PGF_{2\alpha}$ trifluoromethanesulfonamide gave the title compound.

EXAMPLE 9

2,2-Dimethylpropionic acid (1R,2R,3R,4S)-4-hydroxy-2-((S)-(E)-3-hydroxyoct-1-enyl)-3-((Z)-7-methanesulfonamino-7-oxohept-2-enyl)cyclopentyl ester Step 1: Preparation of 11-Pivaloyl $PGF_{2\alpha}$ Methyl Ester Pyridine (2.3 mL, 28.5 mmol) and trimethylacetyl chloride (879 μL, 7.14 mmol) were added to a solution of $PGF_{2\alpha}$ methyl ester (2.63 g, 7.14 mmol) in $CH_2Cl_2$ (100 mL) at 0° C. After 2 h, the reaction was allowed to warm to room temperature. After another 1.5 h, the solution was washed with 10% citric acid (2×) and brine then concentrated in vacuo. The crude residue was purified by flash column chromatography (silica gel, 30% EtOAc/Hex) to afford 1.27 g (41%) of 11-Pivaloyl $PGF_{2\alpha}$ methyl ester.

Step 2: Preparation of 9,15-bis-TBDMS-11-Pivaloyl$PGF_{2\alpha}$ Methyl Ester 2,6-Lutidine (1.36 mL, 11.6 mmol) and tert-butyldimethylsilyl chloride (1.75 g, 11.6 mmol) were added to a solution of 11-Pivaloyl $PGF_{2\alpha}$ methyl ester (1.27 g, 2.91 mmol) in DMF (30 mL). After stirring overnight at room temperature, the reaction was diluted with EtOAc then washed with water (3×) and brine and concentrated in vacuo. Purification of the residue by flash column chromatography (silica gel, 10% EtOAc/Hex) afforded 1.84 g (95%) of 9,15-bis-TBDMS-11-Pivaloyl $PGF_{2\alpha}$ methyl ester.

Step 3: Saponification of 9,15-bis-TBDMS-11-Pivaloyl $PGF_{2\alpha}$ Methyl Ester Lithium hydroxide (5.5 mL of a 0.5 N solution in $H_2O$, 2.75 mmol) was added to a solution of 9,15-bis-TBDMS-11-Pivaloyl $PGF_{2\alpha}$ methyl ester (1.82 g, 2.73 mmol) in THF (5.5 mL) and the solution was heated at 50° C. overnight. The reaction mixture was cooled and acidified with 10% aqueous HCl, then extracted with $CHCl_3$ (3×). The extracts were concentrated in vacuo affording 949 mg (53%) of 9,15-bis-TBDMS-11-Pivaloyl $PGF_{2\alpha}$.

Step 4: Preparation of 9,15-bis-TBDMS-11-Pivaloyl $PGF_{2\alpha}$ Methanesulfonamide In accordance with the procedure described above for example 7, step 3, the use of 9,15-bis-TBDMS-11-Pivaloyl $PGF_{2\alpha}$ a gave 9,15-bis-TBDMS-11-Pivaloyl $PGF_{2\alpha}$ methanesulfonamide.

Step 5: Desilylation of 9,15-bis-TBDMS-11-Pivaloyl $PGF_{2\alpha}$ Methanesulfonamide In accordance with the procedure described in example 7, step 4, the use of 9,15-bis-TBDMS-11-Pivaloyl $PGF_{2\alpha}$ methanesulfonamide gave the title compound. The method of this Example is shown in Scheme 4.

Scheme 4

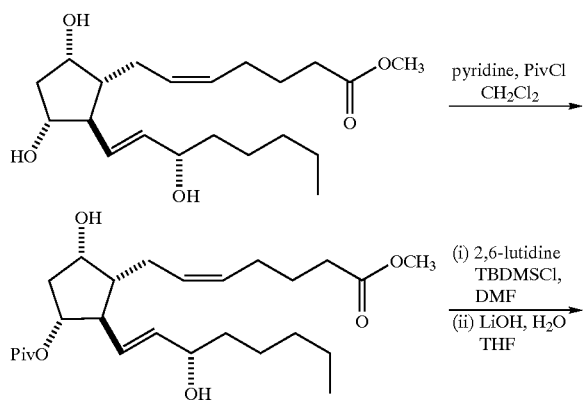

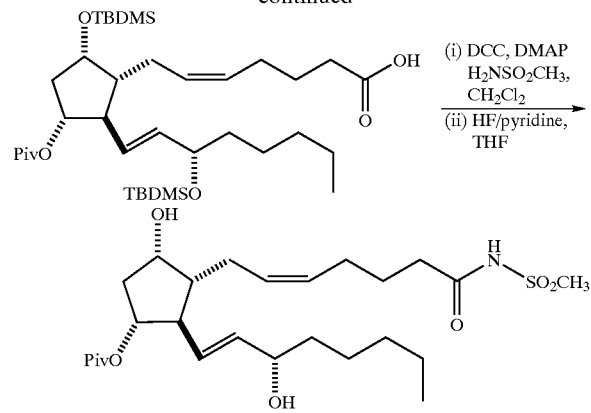

EXAMPLE 10

N-{(E)-7-[(1R,2R,3R,5S)-3,5-Dihydroxy-2-((S)-(E)-3-hydroxy-5-phenylpent-1-enyl)cyclopentyl]hept-5-enoyl}methanesulfonamide Step 1: Preparation of tris-TBDMS-17-phenyl $PGF_{2\alpha}$ Methyl Ester 2,6-Lutidine (2.27 mL, 19.5 mmol) and tert-butyldimethylsilyl chloride (2.94 g, 19.5 mmol) were added to a solution of 17-phenyl $PGF_{2\alpha}$ methyl ester (1.30 g, 3.25 mmol) in DMF (32.5 mL). After stirring overnight at room temperature, the reaction was diluted with EtOAc then washed with water (3×) and brine and concentrated in vacuo. Purification of the residue by flash column chromatography (silica gel, 5% EtOAc/Hex) afforded 1.86 g (77%) of tris-TBDMS-17-phenyl $PGF_{2\alpha}$ methyl ester.

Step 2: Preparation of 5-(E)-tris-TBDMS-17-phenyl $PGF_{2\alpha}$ Methyl Ester

Phenyl disulfide (54 mg, 0.25 mmol) was added to a solution of tris-TBDMS-17-phenyl $PGF_{2\alpha}$ methyl ester (1.86 g, 2.5 mmol) in benzene (20 mL). The solution was irradiated overnight, then concentrated in vacuo to afford 5-(E)-tris-TBDMS-17-phenyl $PGF_{2\alpha}$ methyl ester, which was used without further purification.

Step 3: Saponification of 5-(E)-tris-TBDMS-17-phenyl $PGF_{2\alpha}$ Methyl Ester Lithium hydroxide (5.0 mL of a 0.5 N solution in $H_2O$, 2.5 mmol) was added to a solution of 5-(E)-tris-TBDMS-17-phenyl $PGF_{2\alpha}$ methyl ester (879 mg, 1.18 mmol) in THF (5.0 mL). The solution was heated to 50° C. overnight. The reaction mixture was cooled and acidified with 3 N HCl then extracted with $CHCl_3$ (3×). The extracts were concentrated in vacuo to afford 5-(E)-tris-TBDMS-17-phenyl $PGF_{2\alpha}$ which was used without further purification.

Step 4: Preparation of 5-(E)-tris-TBDMS-17-phenyl $PGF_{2\alpha}$ Acylsulfonamide In accordance with the procedure described in example 7, step 3, the use of 5-(E)-tris-TBDMS-17-phenyl $PGF_{2\alpha}$ afforded 5-(E)-tris-TBDMS-17-phenyl $PGF_{2\alpha}$ acylsulfonamide Step 5: Desilylation of 5-(E)-tris-TBDMS-17-phenyl $PGF_{2\alpha}$ Acylsulfonamide In accordance with the procedure described in example 7, step 4, the use of 5-(E)-tris-TBDMS-17-phenyl $PGF_{2\alpha}$ acylsulfonamide gave the title compound. The method of the Example is shown in Scheme 5.

15

Scheme 5

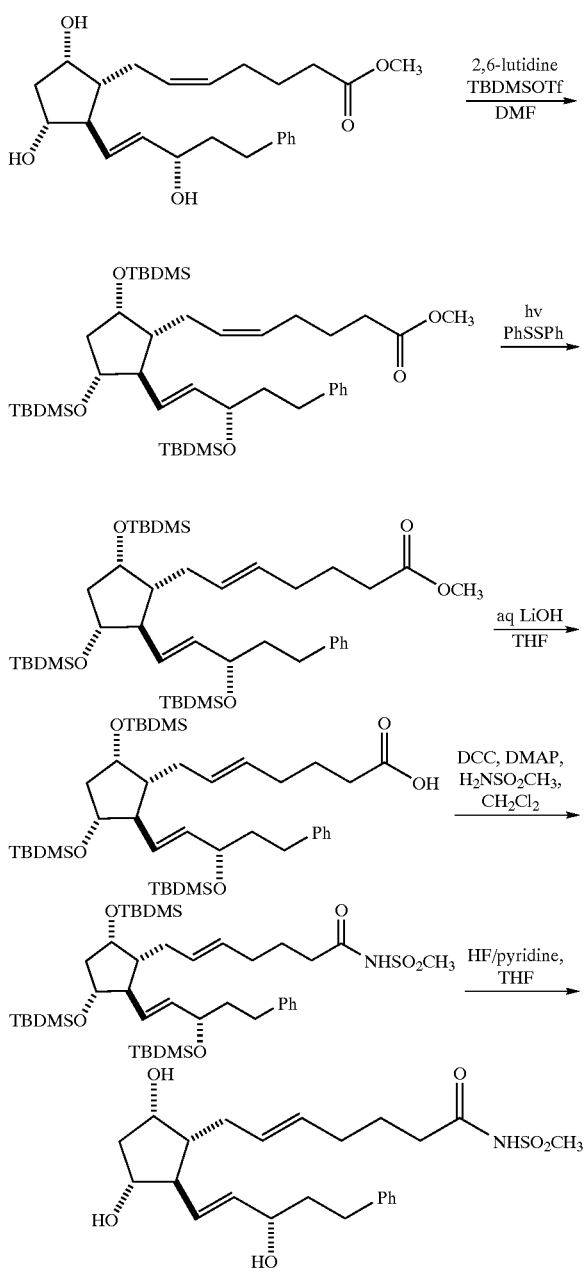

EXAMPLE 11

(Z)-7-[(1R,2R,3R,5S)-2-[(S)-(E)-5-(5-Bromo-4-methylthiophen-2-yl)-3-(tetrahydropyran-2-yloxy)pent-1-enyl]-3,5-bis(tetrahydropyran-2-yloxy)cyclopentyl]hept-5-enoic acid (5a)

Step 1: Preparation of Enone 2a

To a suspension of sodium hydride (60% oil dispersion, 100 mg, 2.50 mmol) in THF (6 mL) at 0° C. was added a solution of dimethyl 4-(5-(2-bromo-3-methyl)thienyl)-2-oxobutylphosphonate (856 mg, 2.41 mmol) in THF (4 mL+2 mL). After 15 min at 0° C., a solution of aldehyde 1 (877 mg, 2.01 mmol) in THF (4 mL+2 mL) was added. After 30 min at 0° C., the reaction was allowed to warm to room temperature. After 2 h at room temperature, the reaction was quenched with saturated aqueous NH$_4$Cl and extracted with EtOAc. The organic phase was washed with saturated aqueous NaHCO$_3$ and brine, then dried (MgSO$_4$), filtered and concentrated in vacuo. Purification of the residue by flash column chromatography (silica gel, 25% EtOAc/Hex) gave 1.15 g (86%) of enone 2a.

16

Step 2: Preparation of 15S Alcohol (3a)

Absolute ethanol (3.75 mL of a 1.0 M solution in THF, 3.75 mmol) was slowly added to a solution of lithium aluminum hydride (3.75 mL of a 1.0 M solution in THF, 3.75 mL). A solution of (S)-1,1'-bi-2-naphthol (1.08 g, 3.77 mmol) in THF (15 mL) was then added dropwise. After 30 min, a cloudy heterogeneous mixture persisted.

The freshly prepared BINAl—H mixture was cooled to −85° C., then a solution of enone 2a (500 mg, 0.75 mmol) in THF (15 mL) was added dropwise. After 1 h at −85° C., the reaction mixture was warmed to −78° C. After 1 h at −78° C., the reaction was quenched with methanol, allowed to warm to room temperature and then 1 N HCl was added. THF was removed by concentration in vacuo, then the aqueous remainder was extracted with EtOAc (2×). The combined extracts were washed with brine then dried (Na$_2$SO$_4$), filtered and concentrated in vacuo. The residue dissolved in CH$_2$Cl$_2$, then (S)-1,1'-bi-2-naphthol was precipitated by addition of hexane. The solid was removed by filtration (800 mg of (S)-1,1'-bi-2-naphthol was recovered) and the filtrate was concentrated in vacuo. Purification of the residue by flash column chromatography (silica gel, 25% EtOAc/Hex) gave 215 mg (43%) of alcohol 3a.

Step 3: Preparation of Tris-THP Ester (4a)

Dihydropyran (300 μL, 3.29 mmol) and PPTs (25 mg, 0.10 mmol) were added sequentially to a solution of alcohol 3a (755 mg, 1.13 mmol) in CH$_2$Cl$_2$ (4 mL). The reaction mixture was stirred overnight at room temperature, then concentrated in vacuo. The residue was diluted with EtOAc, washed with 1 N HCl, water, saturated aqueous NaHCO$_3$ and brine, then dried (MgSO$_4$), filtered and concentrated in vacuo. The resulting product 4a was taken on without further purification. If desired, further purification by flash column chromatography (silica gel, 25% EtOAc/Hex) could be carried out.

Step 4: Saponification of Ester (4a)

Lithium hydroxide (4.5 mL of a 1.0 N solution in water, 4.5 mmol) was added to a solution of ester 4a (approx 1.13 mmol) in THF (11 mL). The reaction was stirred overnight at room temperature then concentrated in vacuo. The aqeous remainder was diluted with water then acidified with 1 N HCl and extracted with CH$_2$Cl$_2$ (2×). The combined extracts were washed with brine, dried (Na$_2$SO$_4$), filtered and concentrated in vacuo. Purification of the residue by flash column chromatography (silica gel, 40% EtOAc/Hex) gave 750 mg (90%) of acid 5a. The method of this Example is shown in Scheme 6.

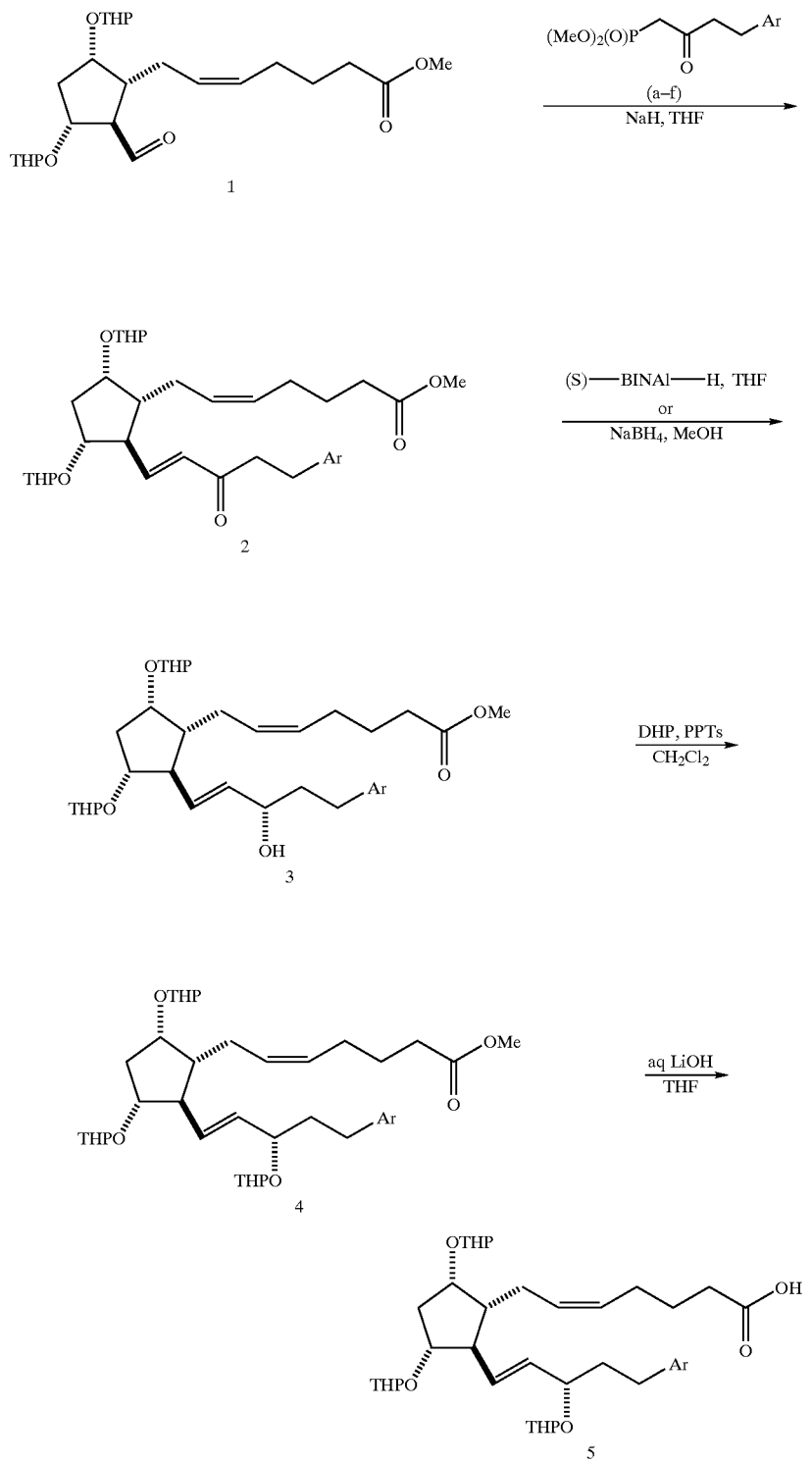
Scheme 6
Ar = 
- 5-bromo-4-methylthiophen-2-yl (a)
- 4-chloro-5-methylthiophen-2-yl (b)
- 5-chlorothiophen-2-yl (c)
- 5-bromothiophen-2-yl (e)
- 2-methylthiophen-3-yl (f)

EXAMPLE 12

(Z)-7-[(1R,2R,3R,5S)-2-[(S)-(E)-5-(4-Chloro-5-methylthiophen-2-yl)-3-(tetrahydropyran-2-yloxy)pent-1-enyl]-3,5-bis(tetrahydropyran-2-yloxy)cyclopentyl]hept-5-enoic acid (5b)

In accordance with the procedures described above for the synthesis of 5a, the use of dimethyl 4-(5-(3-chloro-2-methyl)thienyl)-2-oxobutylphosphonate gave acid 5b.

EXAMPLE 13

(Z)-7-[(1R,2R,3R,5S)-2-[(S)-(E)-5-(5-Chlorothiophen-2-yl)-3-(tetrahydropyran-2-yloxy)pent-1-enyl]-3,5-bis(tetrahydropyran-2-yloxy)cyclopentyl]hept-5-enoic acid (5c)

The synthesis of 5c was carried out in accordance with the procedures described above for the synthesis of 5a, with the following exceptions: dimethyl 4-(5-(2-chloro)thienyl)-2-oxobutylphosphonate) was used in place of dimethyl 4-(5-(2-bromo-3-methyl)thienyl)-2-oxobutylphosphonate and a different reduction method was used in step 2, as described below.

Step 2: Preparation of the 15S Alcohol (3c)

Sodium borohydride (85 mg, 2.25 mmol) was added in one portion to a solution of enone 2c (1.32 g, 2.17 mmol) in MeOH (21 mL) at 0° C. After 3 h, the reaction was concentrated in vacuo then partitioned between saturated aqueous $NH_4Cl$ and EtOAc. The phases were separated and the aqueous phase was extracted with EtOAc. The combined organic phases were dried ($MgSO_4$), filtered and concentrated in vacuo. Purification of the residue by flash column chromatography (3×, silica gel, 25% EtOAc/Hex) afforded 335 mg (25%) of the faster eluting 15R alcohol and 183 mg (14%) of 3c.

EXAMPLE 14

(Z)-7-[(1R,2R,3R,5S)-2-[(S)-(E)-5-(5-Iodothiophen-2-yl)-3-(tert-butyldimethylsilanyoxy)pent-1-enyl]-3,5-bis(tetrahydropyran-2-yloxy)cyclopentyl]hept-5-enoic acid (5d)

In accordance with the procedures described above for the synthesis of 5a, the use of dimethyl 4-(5-(2-iodo)thienyl)-2-oxobutylphosphonate gave enone 2d and alcohol 3d (steps 1 and 2, respectively). Further manipulation of alcohol 3d is as follows:

Step 3: Preparation of 15-TBDMS-bis-THP 4d tert-Butyldimethylsilyl triflate (0.70 mL, 3.06 mmol) was added to a solution of alcohol 3d (718 mg, 1.02 mmol) and 2,6-lutidine (0.60 mL, 5.11 mmol) in $CH_2Cl_2$ (6.0 mL) at 0° C. The reaction was warmed to room temperature and stirred for 12 h. The reaction was quenched with 1 N NaOH and extracted with EtOAc. The organic phase was washed with 1 N HCl, saturated aqueous $NaHCO_3$ and brine then dried ($MgSO_4$), filtered and concentrated in vacuo. Purification of the residue by flash column chromatography (20% EtOAc/Hex) afforded 613 mg (74%) of 4d.

Step 4: Saponification of Ester 4d

In accordance with the procedure described above for the synthesis of 5a, ester 4d gave acid 5d. The method of this Example is shown in Scheme 7.

Scheme 7

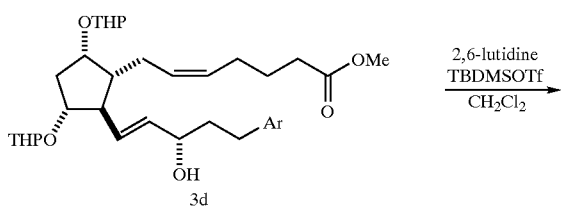

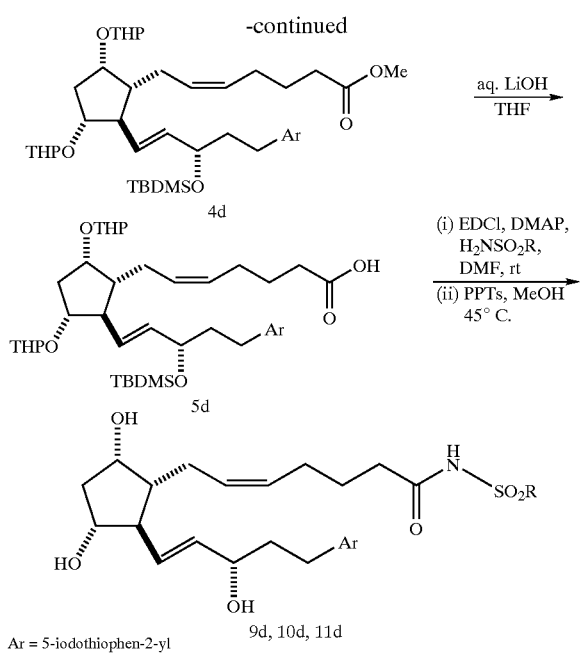

Ar = 5-iodothiophen-2-yl 9d, 10d, 11d

EXAMPLE 15

(Z)-7-[(1R,2R,3R,5S)-2-[(S)-(E)-5-(5-Bromothiophen-2-yl)-3-(tetrahydropyran-2-yloxy)pent-1-enyl]-3,5-bis(tetrahydropyran-2-yloxy)cyclopentyl]hept-5-enoic acid (5e)

In accordance with the procedures described above for the synthesis of 5a, the use of dimethyl 4-(5-(2-bromo)thienyl)-2-oxobutylphosphonate gave acid 5e.

EXAMPLE 16

(Z)-7-[(1R,2R,3R,5S)-2-[(S)-(E)-5-(2-Methylthiophen-3-yl)-3-(tetrahydropyran-2-yloxy)pent-1-enyl]-3,5-bis(tetrahydropyran-2-yloxy)cyclopentyl]hept-5-enoic acid (5f)

In accordance with the procedures described above for the synthesis of 5a, the use of dimethyl 4-(3-(2-methyl)thienyl)-2-oxobutylphosphonate gave acid 5f.

EXAMPLE 17

N-((Z)-7-{(1R,2R,3R,5S)-2-[(S)-(E)-5-(5-Bromo-4-methylthiophen-2-yl)-3-hydroxypent-1-enyl]-3,5-dihydroxycyclopentyl}hept-5-enoyl)methanesulfonamide (9a)

Step 1: Preparation of the Tris-THP Acylsulfonamide (6a)

Acid 5a (100 mg, 0.135 mmol), EDCI (36 mg, 0.19 mmol), DMAP (20 mg, 0.16 mmol) and methanesulfonamide (39 mg, 0.41 mmol) were dissolved in DMF (0.6 mL) and the resulting solution was stirred at room temperature under an atmosphere of nitrogen. After 15 h the solution was diluted with EtOAc and washed with 1 N aqueous HCl (3×) and brine (1×), then dried ($Na_2SO_4$), filtered and concentrated in vacuo. The crude product (6a), judged to be >90% pure by $^1H$ NMR, was used directly in the next step.

Step 2: Deprotection of the Tris-THP Acylsulfonamide (6a)

A solution of 6a (approx. 0.135 mmol) in MeOH (1.1 mL) was treated with PPTs (4 mg, 0.016 mmol). The solution was heated at 45° C. under an atmosphere of nitrogen. After 16 h, the reaction mixture was cooled then concentrated in vacuo to afford a crude oil. Flash column chromatography (silica gel, EtOAc, then 2% MeOH in EtOAc) gave 24 mg (31% for 2 steps) of 9a. The method of this Example is shown in Scheme 8.

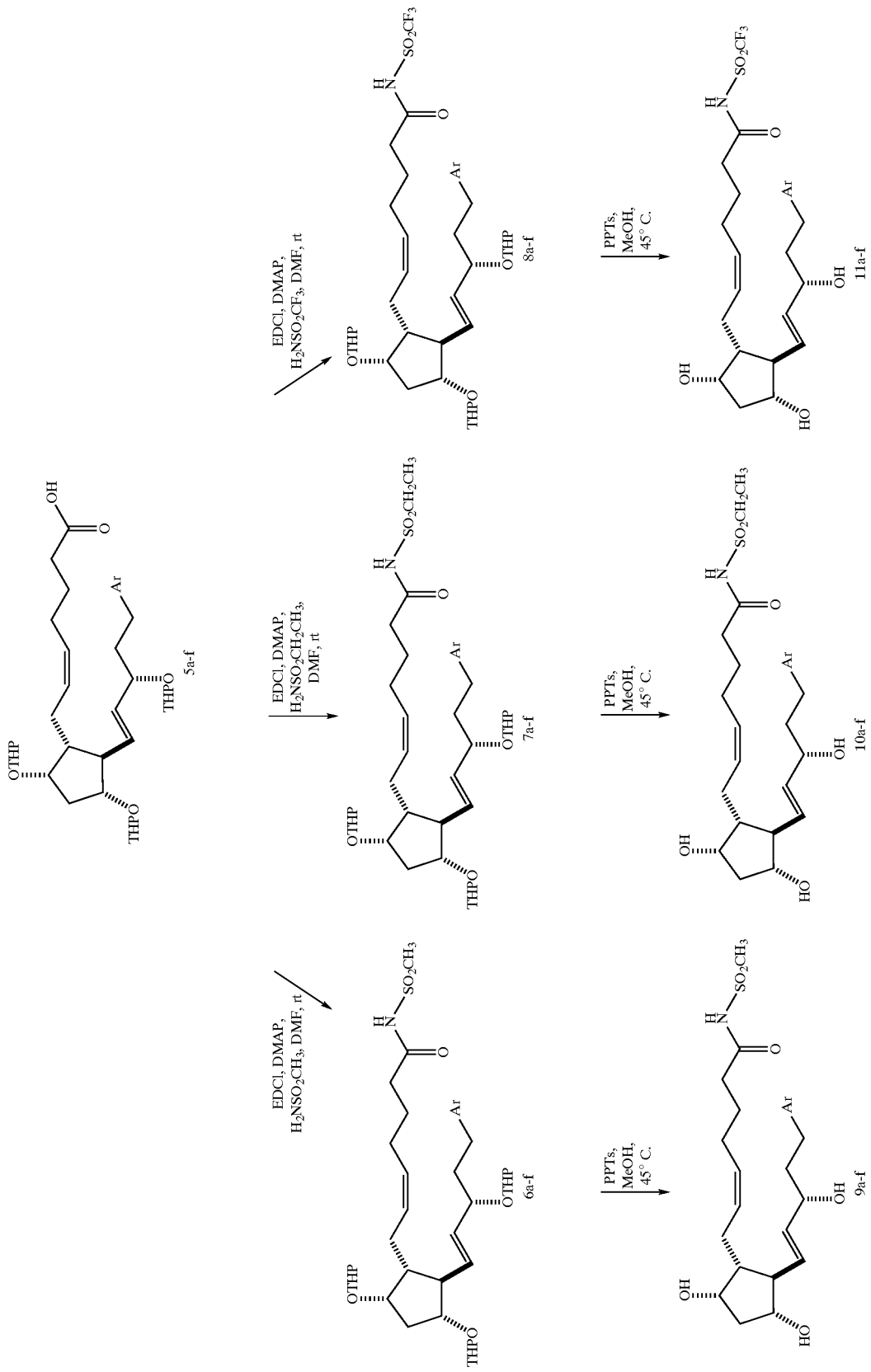

EXAMPLE 18

Ethanesulfonic acid ((Z)-7-{(1R,2R,3R,5S)-2-[(S)-(E)-5-(5-bromo-4-methylthiophen-2-yl)-3-hydroxypent-1-enyl]-3,5-dihydroxycyclopentyl}hept-5-enoyl)amide (10a)

Step 1: Preparation of the Tris-THP Acylsulfonamide (7a)

Acid 5a (100 mg, 0.135 mmol), EDCI (36 mg, 0.19 mmol), DMAP (20 mg, 0.16 mmol) and ethanesulfonamide (45 mg, 0.41 mmol) were dissolved in DMF (0.6 mL) and the resulting solution was stirred at room temperature under an atmosphere of nitrogen. After 24 h the solution was diluted with EtOAc and washed with 1 N aqueous HCl (3×) and brine (1×), then dried (Na$_2$SO$_4$), filtered and concentrated in vacuo. The crude product (7a), judged to be>90% pure by $^1$H NMR, was used directly in the next step.

Step 2: Deprotection of the Tris-THP Acylsulfonamide (7a)

A solution of 7a (approx. 0.135 mmol) in MeOH (1.1 mL) was treated with PPTs (4 mg, 0.016 mmol). The solution was heated at 45° C. under an atmosphere of nitrogen. After 16 h, the reaction mixture was cooled then concentrated in vacuo to afford a crude oil. Flash column chromatography (silica gel, EtOAc, then 2% MeOH in EtOAc) gave 20 mg (26% for 2 steps) of 10a. The method of this Example is also shown in Scheme 8.

EXAMPLE 19

N-((Z)-7-{(1R,2R,3R,5S)-2-[(S)-(E)-5-(5-Bromo-4-methylthiophen-2-yl)-3-hydroxypent-1-enyl]-3,5-dihydroxycyclopentyl}hept-5-enoyl)-1,1,1-trifluoromethanesulfonamide (11 a)

Step 1: Preparation of the Tris-THP Acylsulfonamide (8a)

Acid 5a (100 mg, 0.135 mmol), EDCI (36 mg, 0.19 mmol), DMAP (20 mg, 0.16 mmol) and trifluoromethanesulfonamide (61 mg, 0.41 mmol) were dissolved in DMF (0.6 mL) and the resulting solution was stirred at room temperature under an atmosphere of nitrogen. After 15 h the solution was diluted with EtOAc and washed with 1N aqueous HCl (3×) and brine (1×), then dried (Na$_2$SO$_4$), filtered and concentrated in vacuo. The crude product (8a), judged to be>90% pure by $^1$H NMR, was used directly in the next step.

Step 2: Deprotection of the Tris-THP Acylsulfonamide (8a)

A solution of 8a (approx. 0.135 mmol) in MeOH (1.1 mL) was treated with PPTs (4 mg, 0.016 mmol). The solution was heated at 45° C. under an atmosphere of nitrogen. After 16 h, the reaction mixture was cooled then concentrated in vacuo to afford a crude oil. Flash column chromatography (silica gel, EtOAc, then 2% MeOH in EtOAc) gave 45 mg (54% for 2 steps) of acylsulfonamide 11a. The method of this Example is also shown in Scheme 8.

EXAMPLE 20

N-((Z)-7-{(1R,2R,3R,5S)-2-[(S)-(E)-5-(4-Chloro-5-methylthiophen-2-yl)-3-hydroxypent-1-enyl]-3,5-dihydroxycyclopentyl}hept-5-enoyl)methanesulfonamide (9b)

In accordance with the procedures described above for the synthesis of 9a, the use of acid 5b gave 9b.

EXAMPLE 21

Ethanesulfonic acid ((Z)-7-{(1R,2R,3R,5S)-2-[(S)-(E)-5-(4-chloro-5-methylthiophen-2-yl)-3-hydroxypent-1-enyl]-3,5-dihydroxycyclopentyl}hept-5-enoyl)amide (10b)

In accordance with the procedures described above for the synthesis of 10a, the use of acid 5b (41 mg, 0.059 mmol) afforded 9 mg (29% for 2 steps) of 10b.

EXAMPLE 22

N-((Z)-7-{(1R,2R,3R,5S)-2-[(S)-(E)-5-(4-Chloro-5-methylthiophen-2-yl)-3-hydroxypent-1-enyl]-3,5-dihydroxycyclopentyl}hept-5-enoyl)-1,1,1-trifluoromethanesulfonamide (11b)

In accordance with the procedures described above for the synthesis of 11a, the use of acid 5b (41 mg, 0.059 mmol) gave the desired product 11b along with an impurity. The impure product was then suspended in CH$_2$Cl$_2$ and extracted with 1N NaOH. The organic phase was discarded and the basic aqueous phase was acidified to pH 1 with 1N HCl. The aqueous phase was extracted with EtOAc (3×), then the combined organic extracts were dried (Na$_2$SO$_4$), filtered and concentrated in vacuo to afford 15 mg (44% for 2 steps) of 11b.

EXAMPLE 23

N-((Z)-7-{(1R,2R,3R,5S)-2-[((S)-(E)-5-(5-Chlorothiophen-2-yl)-3-hydroxypent-1-enyl)-3,5-dihydroxycyclopentyl]hept-5-enoyl}methanesulfonamide (9c)

The synthesis of 9c was carried out in accordance with the procedures described above for the synthesis of 9a, with the following exceptions: acid 5c (50 mg, 0.073 mmol) was used in place of acid 5a; intermediate 6c was purified by flash column chromatography (silica gel, 45% EtOAc/Hex) to give 43 mg (77%); and a different hydrolysis method (step 2) was used, as described below.

Purified 6c (43 mg, 0.057 mmol) was dissolved in THF (0.1 mL), H$_2$O (0.1 mL) and acetic acid (0.4 mL). The mixture was heated at 35° C. under nitrogen for 42 h. The mixture was cooled and diluted with EtOAc, washed with water and brine, then dried (Na$_2$SO$_4$), filtered and concentrated in vacuo. Purification by flash column chromatography (silica gel, EtOAc, then 2% MeOH in EtOAc) gave 9 mg (31%) of 9c.

EXAMPLE 24

Ethanesulfonic acid ((Z)-7-{(1R,2R,3R,5S)-2-[(S)-(E)-5-(5-chlorothiophen-2-yl)-3-hydroxypent-1-enyl]-3,5-dihydroxycyclopentyl}hept-5-enoyl)amide (10c)

In accordance with the procedures described above for the synthesis of 10a, the use of acid 5c (100 mg, 0.15 mmol) gave 24 mg (31% for 2 steps) of 10c.

EXAMPLE 25

N-((Z)-7-{(1R,2R,3R,5S)-2-[(S)-(E)-5-(5-Chlorothiophen-2-yl)-3-hydroxypent-1-enyl]-3,5-dihydroxycyclopentyl}hept-5-enoyl)-1,1,1-trifluoromethanesulfonamide (11c)

In accordance with the procedures described above for the synthesis of 11b, the use of acid 5c (100 mg, 0.15 mmol) gave 33 mg (40% for 2 steps) of 11c.

EXAMPLE 26

N-((Z)-7-{(1R,2R,3R,5S)-2-[((S)-(E)-5-(5-Iodothiophen-2-yl)-3-hydroxypent-1-enyl)-3,5-dihydroxycyclopentyl]hept-5-enoyl}methanesulfonamide (9d)

In accordance with the procedures described above for the synthesis of 9a, the use of acid 5d (45 mg, 0.056 mmol) gave 15 mg (45% for 2 steps) of 9d.

EXAMPLE 27

Ethanesulfonic acid ((Z)-7-{(1R,2R,3R,5S)-2-[(S)-(E)-5-(5-iodothiophen-2-yl)-3-hydroxypent-1-enyl]-3,5-dihydroxycyclopentyl}hept-5-enoyl)amide (10d)

In accordance with the procedures described above for the synthesis of 10a, the use of acid 5d (45 mg, 0.056 mmol) gave 10 mg (29% for 2 steps) of 10d.

EXAMPLE 28
N-((Z)-7-{(1R,2R,3R,5S)-2-[(S)-(E)-5-(5-Iodothiophen-2-yl)-3-hydroxypent-1-enyl]-3,5-dihydroxycyclopentyl}hept-5-enoyl)-1,1,1-trifluoromethanesulfonamide (11d)

In accordance with the procedures described above for the synthesis of 11b, the use of acid 5d (45 mg, 0.056 mmol) gave 20 mg (55% for 2 steps) of 11d.

EXAMPLE 29
N-((Z)-7-{(1R,2R,3R,5S)-2-[((S)-(E)-5-(5-Bromothiophen-2-yl)-3-hydroxypent-1-enyl)-3,5-dihydroxycyclopentyl]hept-5-enoyl}methanesulfonamide (9e)

The syntheisis of 9e was carried out in accordance with the procedures described above for the synthesis of 9a, with the following exceptions: acid 5e (200 mg, 0.28 mmol) was used in place of acid 5a; intermediate 6e was purified by flash column chromatography (silica gel, 45% EtOAc/hex) to afford 180 mg (81%) of 6e; deprotection of 6e (36 mg, 0.045 mmol) afforded 13 mg (53%) of 9e.

EXAMPLE 30
Ethanesulfonic acid ((Z)-7-{(1R,2R,3R,5S)-2-[(S)-(E)-5-(5-bromothiophen-2-yl)-3-hydroxypent-1-enyl]-3,5-dihydroxycyclopentyl}hept-5-enoyl)amide (10e)

In accordance with the procedures described above for the synthesis of 10a, the use of acid 5e (45 mg, 0.062 mmol) gave 7 mg (20% for 2 steps) of 10e.

EXAMPLE 31
N-((Z)-7-{(1R,2R,3R,5S)-2-[(S)-(E)-5-(5-Bromothiophen-2-yl)-3-hydroxypent-1-enyl]-3,5-dihydroxycyclopentyl}hept-5-enoyl)-1,1,1-trifluoromethanesulfonamide (11e)

In accordance with the procedures described above for the synthesis of 11b, the use of acid 5e (45 mg, 0.062 mmol) gave 22 mg (59% for 2 steps) of 11e.

EXAMPLE 32
N-((Z)-7-{(1R,2R,3R,5S)-3,5-Dihydroxy-2-[((S)-(E)-3-hydroxy-5-(2-methylthiophen-3-yl)pent-1-enyl)cyclopentyl}hept-5-enoyl)methanesulfonamide (9f)

In accordance with the procedures described above for the synthesis of 9a, the use of acid 5f (200 mg, 0.30 mmol) gave 52 mg (37% for 2 steps) of 9f.

EXAMPLE 33
Ethanesulfonic acid ((Z)-7-{(1R,2R,3R,5S)-3,5-dihydroxy-2-[((S)-(E)-3-hydroxy-5-(2-methylthiophen-3-yl)pent-1-enyl]cyclopentyl}hept-5-enoyl)amide (10f)

In accordance with the procedures described above for the synthesis of 10a, the use of acid 5f (200 mg, 0.30 mmol) afforded 110 mg (73% for 2 steps)of 10f.

EXAMPLE 34
N-((Z)-7-{(1R,2R,3R,5S)-3,5-Dihydroxy-2-[((S)-(E)-3-hydroxy-5-(2-methylthiophen-3-yl)pent-1-enyl]cyclopentyl}hept-5-enoyl)-1,1,1-trifluoromethanesulfonamide (11 f)

According to the procedures above for 11a, the use of acid 5f (111 mg, 0.17 mmol) gave 51 mg (56% for 2 steps) of 11f.

EXAMPLE 35
7-[(1R,2R,3R,5S)-2-[(S)-(E)-5-(2-Methylthiophen-3-yl)-3-(tetrahydropyran-2-yloxy)pent-1-enyl]-3,5-bis(tetrahydropyran-2-yloxy)cyclopentyl]heptanoic acid (13)

Step 1: Preparation of the Partially Saturated Ester 12

Dienyl ester 4f (160 mg, 0.24 mmol) was dissolved in THF (1.0 mL) then tris(triphenylphosphine)rhodium(I) chloride (55 mg, 0.059 mmol) was added. The reaction was evacuated and purged under an atmosphere of hydrogen. After sstirring for 24 h the reaction was concentrated in vacuo. Purification of the crude residue by flash column chromatography (silica gel, 20% EtOAc/hex) afforded 151 mg (94%) of 12.

Step 2: Saponification of Ester 12

A solution of ester 12 (151 mg, 0.22 mmol) in THF (2.2 mL) was treated with lithium hydroxide (0.9 mL of a 1.0N solution in H$_2$O, 0.9 mmol). After 20 h stirring at room temperature, the reaction mixture was concentrated in vacuo, diluted with H$_2$O and acidified to pH 3 with 1N HCl. The aqueous mixture was extracted with EtOAc (2×), then the combined extracts were dried (Na$_2$SO$_4$), filtered and concentrated in vacuo. Purification of the crude residue by flash column chromatography (silica gel, 33% EtOAc/hex) afforded 130 mg (88%) of 13. The method of the Example is shown in Scheme 9.

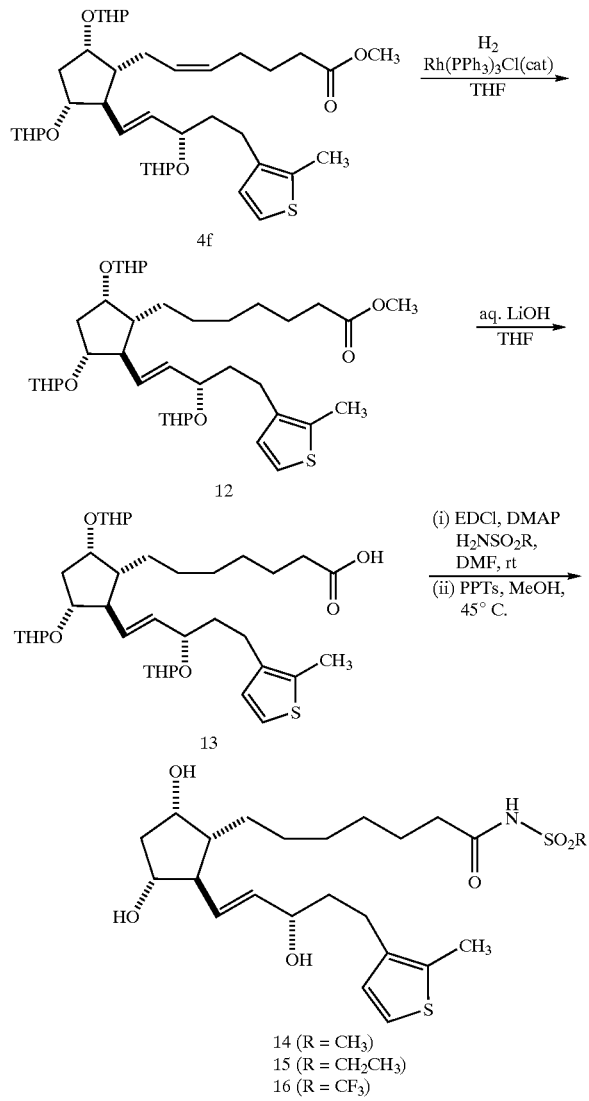

EXAMPLE 36
N-(7-{(1R,2R,3R,5S)-3,5-Dihydroxy-2-[((S)-(E)-3-hydroxy-5-(2-methylthiophen-3-yl)pent-1-enyl)cyclopentyl}heptanoyl)methanesulfonamide (14)

In accordance with the procedures given above for the synthesis of 9a, the use of acid 13 (37 mg, 0.056 mmol) gave 13 mg (48% for 2 steps) of 14. The method of the Example is also shown in Scheme 9.

EXAMPLE 37
Ethanesulfonic acid (7-{(1R,2R,3R,5S)-3,5-dihydroxy-2-[((S)-(E)-3-hydroxy-5-(2-methylthiophen-3-yl)pent-1-enyl)cyclopentyl}heptanoyl)amide (15)

In accordance with the procedures given above for the synthesis of 10a, the use of acid 13 (37 mg, 0.056 mmol) gave 9 mg (32% for 2 steps) of 15.

EXAMPLE 38
N-(7-{(1R,2R,3R,5S)-3,5-Dihydroxy-2-[((S)-(E)-3-hydroxy-5-(2-methylthiophen-3-yl)pent-1-enyl]cyclopentyl}heptanoyl)-1,1,1-trifluoromethanesulfonamide (16)

In accordance with the procedures given above for the synthesis of 11b, the use of acid 13 (37 mg, 0.056 mmol) gave 14 mg (46% for 2 steps) of 16.

EXAMPLE 39
Acetic acid ({(Z)-7-[(1R,2R,3R,5S)-3,5-dihydroxy-2-((S)-(E)-3-hydroxyoct-1-enyl)-cyclopentyl]hept-5-enoyl}methanesulfonylamino)methyl Ester (17g)

Step 1: Preparation of the THP-Protected Prodrug

Diisopropropylethylamine (0.23 mL, 1.32 mmol) and bromomethyl acetate (0.11 mL, 1.12 mmol) were added sequentially to a solution of 6g (110 mg, 0.161 mmol) in DMF (1.0 mL) and the resulting solution was stirred at room temperature under an atmosphere of nitrogen overnight. The solution was concentrated in vacuo. Purification of the crude residue by flash column chromatography (silica gel, 35% EtOAc/hex) afforded 109 mg (90%) of the THP protected prodrug.

Step 2: Deprotection of the THP-Protected Prodrug

A solution of the THP-protected prodrug (109 mg, 0.144 mmol) in MeOH (1.5 mL) was treated with PPTs (8 mg, 0.032 mmol). The solution was heated at 45° C. under an atmosphere of nitrogen. After 16 h, the reaction mixture was cooled then concentrated in vacuo to afford a crude oil. Flash column chromatography (silica gel, EtOAc, then 2% MeOH in EtOAc) gave 47 mg (65%) of 17g. See FIG. 2.

EXAMPLE 40
2,2-Dimethylpropionic acid ({(Z)-7-[(1R,2R,3R,5S)-3,5-dihydroxy-2-((S)-(E)-3-hydroxyoct-1-enyl)-cyclopentyl]hept-5-enoyl}methanesulfonylamino)methyl Ester (18g)

Step 1: Preparation of the THP-Protected Prodrug

Diisopropropylethylamine (0.25 mL, 1.44 mmol), sodium iodide (187 mg, 1.25 mmol) and chloromethyl pivalate (0.18 mL, 1.25 mmol) were added sequentially to a solution of 6g (121 mg, 0.177 mmol) in DMF (1.1 mL) and the resulting mixture was stirred at room temperature under an atmosphere of nitrogen overnight. The reaction mixture was diluted with EtOAc, washed with brine (3×), dried ($Na_2SO_4$), filtered and concentrated in vacuo. Purification of the crude residue by flash column chromatography (silica gel, 25% EtOAc/hex) afforded 94 mg (67%) of the THP protected prodrug.

Step 2: Deprotection of the THP-Protected Prodrug

A solution of the crude THP-protected acylsulfonamide derivative (93 mg, 0.117 mmol) in MeOH (1.2 mL) was treated with PPTs (7 mg, 0.028 mmol). The solution was heated at 45° C. under an atmosphere of nitrogen. After 24 h, the reaction mixture was cooled then concentrated in vacuo to afford a crude oil. Flash column chromatography (silica gel, 100% EtOAc, then 2% MeOH in EtOAc) gave 47 mg (65%) of 18g. See FIG. 3.

EXAMPLE 41
Acetic acid [((Z)-7-{(1R,2R,3R,5S)-2-[((S)-(E)-5-(5-bromo-4-methylthiophen-2-yl)-3-hydroxypent-1-enyl)-3,5-dihydroxycyclopentyl}hept-5-enoyl)methanesulfonyl-amino] Methyl Ester (17a)

In accordance with the procedures given above for the synthesis of 17g, the use of 6a (70 mg, 0.086 mmol) gave 21 mg (38% for 2 steps) of 17a. See FIG. 2.

EXAMPLE 42
2,2-Dimethylpropionic acid [((Z)-7-{(1R,2R,3R,5S)-2-[((S)-(E)-5-(5-bromo-4-methylthiophen-2-yl)-3-hydroxypent-1-enyl)-3,5-dihydroxycyclopentyl}hept-5-enoyl)methanesulfonyl-amino] Methyl Ester (18a)

In accordance with the procedures given above for the synthesis of 18g, the use of 6a (78 mg, 0.95 mmol) gave 28 mg (43% for 2 steps) of 18a. See FIG. 3.

EXAMPLE 43
Acetic acid [((Z)-7-{(1R,2R,3R,5S)-2-[((S)-(E)-5-(4-chloro-5-methylthiophen-2-yl)-3-hydroxypent-1-enyl)-3,5-dihydroxycyclopentyl}hept-5-enoyl)methanesulfonyl-amino] Methyl Ester (17b)

In accordance with the procedures given above for the synthesis of 17g, the use of 6b (60 mg, 0.078 mmol) gave 28 mg (61% for 2 steps) of 17b. See FIG. 2.

EXAMPLE 44
2,2-Dimethylpropionic acid [((Z)-7-{(1R,2R,3R,5S)-2-[((S)-(E)-5-(4-chloro-5-methyl-thiophen-2-yl)-3-hydroxypent-1-enyl)-3,5-dihydroxycyclopentyl}hept-5-enoyl)methane-sulfonyl-amino] Methyl Ester (18b)

In accordance with the procedures given above for the synthesis of 18g, the use of 6b (60 mg, 0.078 mmol) gave 33 mg (67% for 2 steps) of 18b. See FIG. 3.

EXAMPLE 45
Acetic acid [((Z)-7-{(1R,2R,3R,5S)-2-[((S)-(E)-5-(5-bromothiophen-2-yl)-3-hydroxypent-1-enyl)-3,5-dihydroxycyclopentyl}hept-5-enoyl)methanesulfonylamino] Methyl Ester (17e)

In accordance with the procedures given above for the synthesis of 17g, the use of 6e (72 mg, 0.090 mmol) gave 35 mg (63% for 2 steps) of 17e. See FIG. 2.

EXAMPLE 46
2,2-Dimethylpropionic acid [((Z)-7-{(1R,2R,3R,5S)-2-[((S)-(E)-5-(5-bromothiophen-2-yl)-3-hydroxypent-1-enyl)-3,5-dihydroxycyclopentyl}hept-5-enoyl)methanesulfonyl-amino] Methyl Ester (18e)

In accordance with the procedures given above for the synthesis of 18g, the use of 6e (72 mg, 0.090 mmol) gave 38 mg (64% for 2 steps) of 18e. See FIG. 3.

EXAMPLE 47
N-{(Z)-7-[(1R,2R,3R,5S)-3,5-Dihydroxy-2-((S)-(E)-3-hydroxyoct-1-enyl)cyclopentyl]-hept-5-enoyl}benzenesulfonamide (19g)

Step 1: Preparation of the Tris-THP Benzenesulfonamide

Tris-THP $PGF_{2\alpha}$ (150 mg, 0.255 mmol), EDCI (69 mg, 0.36 mmol), DMAP (37 mg, 0.30 mmol) and benzenesulfonamide (120 mg, 0.763 mmol) were dissolved in DMF (1.2 mL) and the resulting solution was stirred at room temperature under an atmosphere of nitrogen. After 15 h the solution was diluted with EtOAc and washed with 1 N aqueous HCl (3×) and brine (1×), then dried ($Na_2SO_4$), filtered and concentrated in vacuo to afford a crude oil. Flash column chromatography (silica gel, 40% EtOAc/Hex) gave 150 mg (79%) of tris-THP $PGF_{2\alpha}$ benzenesulfonamide.

Step 2: Deprotection of the Tris-THP Benzenesulfonamide

A solution of tris-THP $PGF_{2\alpha}$ benzenesulfonamide (150 mg, 0.201 mmol) in MeOH (2.0 mL) was treated with PPTs (10 mg, 0.040 mmol). The solution was heated at 45° C. under an atmosphere of nitrogen. After 16 h, the reaction mixture was cooled then concentrated in vacuo to afford a crude oil. Flash column chromatography (silica gel, EtOAc, then 2% MeOH in EtOAc) gave 48 mg (48% for 2 steps) of 19g. See FIG. 4.

EXAMPLE 48

N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}benzenesulfonamide (19b)

In accordance with the procedures given above for the synthesis of 19g, the use of 5b (125 mg, 0.175 mmol) gave 50 mg (49% for 2 steps) of 19b. See FIG. 4.

The effects of the compounds of this invention on intraocular pressure are also provided in the following tables. The compounds were prepared at the said concentrations in a vehicle comprising 0.1% polysorbate 80 and 10 mM TRIS base. Dogs were treated by administering 25 μl to the ocular surface, the contralateral eye received vehicle as a control. Intraocular pressure was measured by applanation pneumatonometry. Dog intraocular pressure was measured immediately before drug administration and at 6 hours thereafter.

Compounds 9a, 9b, 9c, 9e, 10a, 18a, and 19b were examined and showed a pronounced ocular hypotensive effect in dogs.

| Compound # | IOP max % decrease time (Hr) | IOP max mmHg time (Hr) |
|---|---|---|
| 9a | −13.6% (72 hr): 0.03% | −2.8 (72 hr): 0.03% |
| 9b | −26.5 (96 hr): 0.03% | −4.9 (96 hr): 0.03% |
| 9c | −23.8% (102 hr): 0.03% | −4.2 (102 hr): 0.03% |
| 9e | −11.7% (100 hr): 0.03% | −2.0 (100 hr): 0.03% |
| 10a | −24.9% (4 hr): 0.03% | −5.1 (4 hr): 0.03% |
| 18a | −22.0 (24 hr): 0.03% | −3.9 (24 hr): 0.03% |
| 19b | −13.0% (74 hr): 0.03% | −2.6 (74 hr): 0.03% |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

What is claimed is:

1. A novel compound represented by the general formula I;

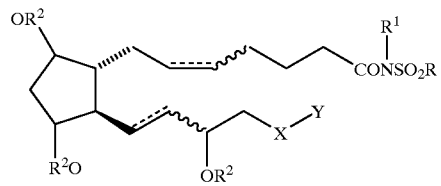

wherein a hatched line represents the α configuration, a triangle represents the β configuration, a straight line, e.g. at the 9, 11 or 15 position represents either the α or β configuration, a dotted line represents the presence or absence of a double bond; a wavy line represents a cis or trans bond;

X is $(CH_2)_n$;

n is 0 or an integer of from 1 to 4;

Y is $C_1$–$C_5$ n-alkyl, $C_3$–$C_7$ cycloalkyl, phenyl, furanyl, thienyl, pyridinyl, thiazolyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $N(R^2)_2$, $CO_2R^2$ and $OR^2$;

Z is $(CH_2)_n$ or a covalent bond;

R is $C_1$–$C_6$ lower alkyl, benzyl or Z-$CF_3$ or mesylate or triflate;

$R^1$ is H, $R^2$ or $COR^2$;

$R^2$ is H or $C_1$–$C_5$ lower alkvl or 9, 11 or 15 esters thereof; provided however, said compound is not N-{(Z)-7-[(1R,2R,3R,5S)-3,5-Dihydroxy-2-((S)-(E)-3-hydroxyoct-1-enyl)cyclopentyl]-hept-5-enoyl}methanesulfonamide, N-{(Z)-7-[(1R,2R,3R,5S)-3,5-Dihydroxy-2-((S)-(E)-3-hydroxy-5-phenylpent-1-enyl)cyclopentyl]-hept-5-enoyl}methanesulfonamide, or N-{(Z)-7-[(1R,2R,3R,5S)-3,5-Dihydroxy-2-((S)-(E)-3-hydroxyoct-1-enyl)cyclopentyl]-hept-5-enoyl}benzenesulfonamide.

2. The compound according to claim 1 wherein said compound is represented by the general formula II;

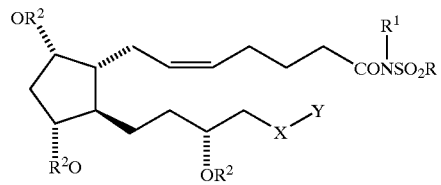

3. The compound according to claim 2 wherein said compound is represented by the general formula III;

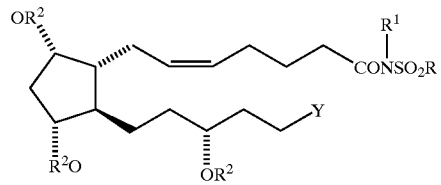

4. The compound of claim 2 wherein Y is selected from the group consisting of n-propyl, thienyl and halo or lower $C_1$ to $C_4$ alkyl substituted derivatives of thienyl.

5. The compound of claim 2 wherein Z is a covalent bond.

6. The compound of claim 5 wherein R is selected from the group consisting methyl, ethyl, n-propyl, n-butyl, $CF_3$, mesylate and triflate.

7. The compound of claim 5 wherein $R^1$ is H, methyl, ethyl, acetyl and pivaloyl.

8. The compound of claim 5 wherein $R^2$ is H.

9. The compound of claim 1 wherein said compound is selected from the group consisting of;

Ethanesulfonic acid {(Z)-7-[(1R,2R,3R,5S)-3,5-dihydroxy-2-((S)-(E)-3-hydroxyoct-1-enyl)cyclopentyl]hept-5-enoyl}amide Ethanesulfonic acid {(Z)-7-[(1R,2R,3R,5S)-3,5-dihydroxy-2-((R)-(E)-3-hydroxyoct-1-enyl)cyclopentyl]hept-5-enoyl}amide Propane-1-sulfonic acid {(Z)-7-[(1R,2R,3R,5S)-3,5-dihydroxy-2-((S)-(E)-3-hydroxyoct-1-enyl)cyclopentyl]hept-5-enoyl}amide Propane-1-sulfonic acid {(Z)-7-[(1R,2R,3R,5S)-3,5-dihydroxy-2-((R)-(E)-3-hydroxyoct-1-enyl)cyclopentyl]hept-5-enoyl}amide Butane-1-sulfonic acid {(Z)-7-[(1R,2R,3R,5S)-3,5-dihydroxy-2-((S)-(E)-3-hydroxyoct-1-enyl)cyclopentyl]hept-5-enoyl}amide Butane-1-sulfonic acid {(Z)-7-[(1R,2R,3R,5S)-3,5-dihydroxy-2-((R)-(E)-3-hydroxyoct-1-enyl)cyclopentyl]hept-5-enoyl}amide N-{(Z)-7-[(1R,2R,3R,5S)-3,5-Dihydroxy-2-((S)-(E)-3-hydroxyoct-1-enyl)cyclopentyl]-hept-5-enoyl}N-methylmethanesulfonamide N-{(Z)-7-[(1R,2R,3R,5S)-3,5-Dihydroxy-2-((S)-(E)-3-hydroxyoct-1-enyl)cyclopentyl]-hept-5-enoyl}N-ethylmethanesulfonamide 2,2-Dimethylpropionic acid (1R,2R,3R,5S)-4-hydroxy-2-((S)-(E)-3-hydroxyoct-1-enyl)-3-((Z)-7-methanesulfonylamino-7-oxohept-2-enyl)cyclopentyl ester N-{(Z)-7-[(1R,2R,3R,5S)-3,5-Dihydroxy-2-((S)-(E)-3-hydroxyoct-1-enyl)cyclopentyl]-hept-5-enoyl}-1,1,1-trifluoromethanesulfonamide N-{(E)-7-[(1R,2R,3R,5S)-3,5-Dihydroxy-2-((S)-(E)-3-hydroxy-5-phenylpent-1-enyl)-cyclopentyl]hept-5-enoyl}methanesulfonamide Ethanesulfonic acid ((Z)-7-{(1R,2R,3R,5S)-2-[(S)-(E)-5-(4-bromo-5-methylthiophen-2-yl)-3-hydroxypent-1-enyl]-3,5-dihydroxycyclopentyl}hept-5-enoyl)amide N-((Z)-7-{(1R,2R,3R,5S)-2-((S)-(E)-5-(5-Bromo-4-methylthiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-((S)-(E)-5-(5-bromo-4-methylthiophen-2-yl)-3-hydroxypent-1-enyl)-3,5-dihydroxycyclopentyl]hept-5-enoyl}amide N-((Z)-7-{(1R,2R,3R,5S)-2-[((S)-(E)-5-(5-Bromo-4-methylthiophen-2-yl)-3-hydroxypent-1-enyl)-3,5-dihydroxycyclopentyl]hept-5-enoyl}-1,1,1-trifluoromethanesulfonamide N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-[((S)-(E)-5-(4-chloro-5-methylthiophen-2-yl)-3-hydroxypent-1-enyl)-3,5-dihydroxycyclopentyl]hept-5-enoyl}amide N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}-1,1,1-trifluoromethanesulfonamide N-((Z)-7-{(1R,2R,3R,5S)-3,5-Dihydroxy-2-[((S)-(E)-3-hydroxy-5-(2-methylthiophen-3-yl)pent-1-enyl)cyclopentyl}hept-5-enoyl)methanesulfonamide Ethanesulfonic acid ((Z)-7-{(1R,2R,3R,5S)-3,5-dihydroxy-2-[((S)-(E)-3-hydroxy-5-(2-methylthiophen-3-yl)pent-1-enyl]cyclopentyl}hept-5-enoyl)amide N-((Z)-7-{(1R,2R,3R,5S)-3,5-Dihydroxy-2-[((S)-(E)-3-hydroxy-5-(2-methylthiophen-3-yl)pent-1-enyl]cyclopentyl}hept-5-enoyl)-1,1,1-trifluoromethanesulfonamide N-((Z)-7-{(1R,2R,3R,5S)-3,5-Dihydroxy-2-[((S)-(E)-3-hydroxy-5-(2-methylthiophen-3-yl)pent-1-enyl)cyclopentyl}heptanoyl)methanesulfonamide Ethanesulfonic acid ((Z)-7-{(1R,2R,3R,5S)-3,5-dihydroxy-2-[((S)-(E)-3-hydroxy-5-(2-methylthiophen-3-yl)pent-1-enyl]cyclopentyl}heptanoyl)amide N-((Z)-7-{(1R,2R,3R,5S)-3,5-Dihydroxy-2-[((S)-(E)-3-hydroxy-5-(2-methylthiophen-3-yl)pent-1-enyl]cyclopentyl}heptanoyl)-1,1,1-trifluoromethanesulfonamide N-((Z)-7-{(1R,2R,3R,5S)-2-[((S)-(E)-5-(5-Chlorothiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-[((S)-(E)-5-(5-chlorothiophen-2-yl)-3-hydroxypent-1-enyl)-3,5-dihydroxycyclopentyl]hept-5-enoyl}amide N-((Z)-7-{(1R,2R,3R,5S)-2-[((S)-(E)-5-(5-Chlorothiophen-2-yl)-3-hydroxypent-1-enyl)-3,5-dihydroxycyclopentyl]hept-5-enoyl}-1,1,1-trifluoromethanesulfonamide N-((Z)-7-{(1R,2R,3R,5S)-3,5-Dihydroxy-2-[((S)-(E)-3-hydroxy-5-(5-iodothiophen-2-yl)pent-1-enyl)cyclopentyl}heptanoyl)methanesulfonamide Ethanesulfonic acid ((Z)-7-{(1R,2R,3R,5S)-3,5-dihydroxy-2-[((S)-(E)-3-hydroxy-5-(5-iodothiophen-2-yl)pent-1-enyl]cyclopentyl}heptanoyl)amide N-((Z)-7-{(1R,2R,3R,5S)-3,5-Dihydroxy-2-[((S)-(E)-3-hydroxy-5-(5-iodothiophen-2-yl)pent-1-enyl]cyclopentyl}heptanoyl)-1,1,1-trifluoromethanesulfonamide N-((Z)-7-{(1R,2R,3R,5S)-2-[((S)-(E)-5-(5-Bromothiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-[((S)-(E)-5-(5-bromothiophen-2-yl)-3-hydroxypent-1-enyl)-3,5-dihydroxycyclopentyl]hept-5-enoyl}amide N-((Z)-7-{(1R,2R,3R,5S)-2-[((S)-(E)-5-(5-Bromothiophen-2-yl)-3-hydroxypent-1-enyl)-3,5-dihydroxycyclopentyl]hept-5-enoyl}-1,1,1-trifluoromethanesulfonamide Acetic acid ({(Z)-7-[(1R,2R,3R,5S)-3,5-dihydroxy-2-((S)-(E)-3-hydroxyoct-1-enyl)-cyclopentyl]hept-5-enoyl}methanesulfonylamino)methyl ester 2,2-Dimethylpropionic acid ({(Z)-7-[(1R,2R,3R,5S)-3,5-dihydroxy-2-((S)-(E)-3-hydroxyoct-1-enyl)- cyclopentyl]hept-5-enoyl}methanesulfonylamino) methyl ester

Acetic acid [((Z)-7-{(1R,2R,3R,5S)-2-[((S)-(E)-5-(5-bromo-4-methylthiophen-2-yl)-3-hydroxypent-1-enyl)-3,5-dihydroxycyclopentyl}hept-5-enoyl) methanesulfonyl-amino] methyl ester 2,2-Dimethylpropionic acid [((Z)-7-{(1R,2R,3R,5S)-2-[((S)-(E)-5-(5-bromo-4-methylthiophen-2-yl)-3-hydroxypent-1-enyl)-3,5-dihydroxycyclopentyl}hept-5-enoyl)methanesulfonyl-amino] methyl ester Acetic acid [((Z)-7-{(1R,2R,3R,5S)-2-[((S)-(E)-5-(4-chloro-5-methylthiophen-2-yl)-3-hydroxypent-1-enyl)-3,5-dihydroxycyclopentyl}hept-5-enoyl) methanesulfonyl-amino] methyl ester 2,2-Dimethylpropionic acid [((Z)-7-{(1R,2R,3R,5S)-2-[((S)-(E)-5-(4-chloro-5-methyl-thiophen-2-yl)-3-hydroxypent-1-enyl)-3,5-dihydroxycyclopentyl}hept-5-enoyl)methane-sulfonyl-amino] methyl ester Acetic acid [((Z)-7-{(1R,2R,3R,5S)-2-[((S)-(E)-5-(5-bromothiophen-2-yl)-3-hydroxypent-1-enyl)-3,5-dihydroxycyclopentyl}hept-5-enoyl)methanesulfonyl-amino] methyl ester and 2,2-Dimethylpropionic acid [((Z)-7-{(1R,2R,3R,5S)-2-[((S)-(E)-5-(5-bromothiophen-2-yl)-3-hydroxypent-1-enyl)-3,5-dihydroxycyclopentyl}hept-5-enoyl) methanesulfonyl-amino] methyl ester and N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}benzenesulfonamide.

10. The novel compound of claim 9 wherein said compound is selected from the group consisting of;

N-((Z)-7-{(1R,2R,3R,5S)-2-[(S)-(E)-5-(5-Bromo-4-methylthiophen-2-yl)-3-hydroxypent-1-enyl]-3,5-dihydroxycyclopentyl}hept-5-enoyl) methanesulfonamide N-((Z)-7-{(1R,2R,3R,5S)-2-[(S)-(E)-5-(4-Chloro-5-methylthiophen-2-yl)-3-hydroxypent-1-enyl]-3,5-dihydroxycyclopentyl}hept-5-enoyl) methanesulfonamide N-((Z)-7-{(1R,2R,3R,5S)-2-[((S)-(E)-5-(5-Chlorothiophen-2-yl)-3-hydroxypent-1-enyl)-3,5-dihydroxycyclopentyl]hept-5-enoyl}methanesulfonamide N-((Z)-7-{(1R,2R,3R,5S)-2-[((S)-(E)-5-(5-Bromothiophen-2-yl)-3-hydroxypent-1-enyl)-3,5-dihydroxycyclopentyl]hept-5-enoyl}methanesulfonamide Ethanesulfonic acid ((Z)-7-{(1R,2R,3R,5S)-2-[(S)-(E)-5-(5-bromo-4-methylthiophen-2-yl)-3-hydroxypent-1-enyl]-3,5-dihydroxycyclopentyl}hept-5-enoyl)amide 2,2-Dimethylpropionic acid [((Z)-7-{(1R,2R,3R,5S)-2-[((S)-(E)-5-(5-bromo-4-methylthiophen-2-yl)-3-hydroxypent-1-enyl)-3,5-dihydroxycyclopentyl}hept-5-enoyl)methanesulfonyl-amino] methyl ester and N-((Z)-7-{(1R,2R,3R,5S)-2-[((S)-(E)-5-(4-Chloro-5-methylthiophen-2-yl)-3-hydroxypent-1-enyl)-3,5-dihydroxycyclopentyl]hept-5-enoyl}benzenesulfonamide.

11. The novel compound of claim 1 wherein Y is thienyl substituted with at least one of chloro or bromo.

* * * * *